US010584306B2

(12) United States Patent
Long et al.

(10) Patent No.: US 10,584,306 B2
(45) Date of Patent: Mar. 10, 2020

(54) SURFACTANT MICROEMULSIONS

(71) Applicant: Novus International Inc., St. Charles, MO (US)

(72) Inventors: Scott Long, St. Charles, MO (US); Graciela Arhancet, St. Charles, MO (US); Brian Grady, Norman, OK (US); Jeff Harwell, Norman, OK (US); Guangzhe Yu, Norman, OK (US)

(73) Assignees: Board of Regents of the University of Oklahoma, Norman, OK (US); Novus International, Inc., St. Charles, MO (US)

( * ) Notice: Subject to any disclaimer, the term of this patent is extended or adjusted under 35 U.S.C. 154(b) by 0 days.

(21) Appl. No.: 15/675,277

(22) Filed: Aug. 11, 2017

(65) Prior Publication Data

US 2019/0048287 A1 Feb. 14, 2019

(51) Int. Cl.
| | | |
|---|---|---|
| C11D 1/755 | (2006.01) | |
| A61K 8/06 | (2006.01) | |
| A61Q 19/10 | (2006.01) | |
| A61Q 5/02 | (2006.01) | |
| A61K 8/46 | (2006.01) | |
| C11D 17/00 | (2006.01) | |

(52) U.S. Cl.
CPC .............. *C11D 1/755* (2013.01); *A61K 8/068* (2013.01); *A61K 8/46* (2013.01); *A61Q 5/02* (2013.01); *A61Q 19/10* (2013.01); *C11D 17/0021* (2013.01)

(58) Field of Classification Search
CPC .... C11D 1/755; C11D 17/0021; A61Q 19/10; A61Q 5/02; A61K 8/068; A61K 8/46
See application file for complete search history.

(56) References Cited

U.S. PATENT DOCUMENTS

| | | | |
|---|---|---|---|
| 2,703,316 A | 3/1955 | Schneider | |
| 2,787,595 A | 4/1957 | Webb | |
| 2,848,466 A | 8/1958 | Fletcher | |
| 3,272,860 A | 9/1966 | Nufer | |
| 3,288,859 A | 11/1966 | Lyness et al. | |
| 3,290,254 A | 12/1966 | Anderson | |
| 3,329,617 A | 7/1967 | Doering | |
| 3,761,518 A | 9/1973 | Haglid | |
| 3,773,927 A | 11/1973 | Cummins | |
| 3,806,529 A | 4/1974 | Havinga et al. | |
| 4,033,938 A | 7/1977 | Augurt et al. | |
| 4,095,029 A | 6/1978 | Fields | |
| 4,130,532 A | 12/1978 | Lamb | |
| 4,133,794 A | 1/1979 | Lamb | |
| 4,235,942 A | 11/1980 | Heller et al. | |
| 4,310,690 A | 1/1982 | Cummins | |
| 4,317,779 A | 3/1982 | Crawford | |
| 4,353,942 A | 10/1982 | Carey | |
| 4,388,327 A | 6/1983 | Cummins | |
| 4,395,363 A | 7/1983 | Crawford | |
| 4,419,198 A | 12/1983 | Breda et al. | |
| 4,435,527 A | 3/1984 | Cuscurida | |
| 4,451,486 A | 5/1984 | Baker et al. | |
| 4,464,292 A | 8/1984 | Lengyel | |
| 4,524,077 A | 6/1985 | Ruest et al. | |
| 4,579,962 A | 4/1986 | Takano | |
| 4,720,484 A | 1/1988 | Vincent et al. | |
| 4,727,163 A | 2/1988 | Bellis | |
| 4,749,811 A | 6/1988 | Cesa et al. | |
| 4,777,289 A | 10/1988 | Ruest | |
| 4,794,187 A | 12/1988 | Glossmann | |
| 4,797,426 A | 1/1989 | Waki et al. | |
| 4,808,622 A | 2/1989 | Kinast et al. | |
| 4,835,293 A | 5/1989 | Bhatia | |
| 4,855,495 A | 8/1989 | Takano | |
| 4,883,911 A | 11/1989 | Ruest | |
| 5,061,710 A | 10/1991 | Haslanger et al. | |
| 5,274,073 A | 12/1993 | Gruber et al. | |
| 5,294,605 A | 3/1994 | Houghten et al. | |
| 5,310,599 A | 5/1994 | Ford et al. | |
| 5,326,887 A | 7/1994 | Di Cosimo et al. | |
| 5,348,978 A | 9/1994 | Baxter et al. | |
| 5,357,001 A | 10/1994 | Grosse-Bley et al. | |
| 5,399,665 A | 3/1995 | Barrera et al. | |
| 5,405,991 A | 4/1995 | Feist et al. | |
| 5,503,852 A | 4/1996 | Steiner et al. | |
| 5,602,229 A | 2/1997 | Malabarba et al. | |
| 6,008,261 A | 12/1999 | Genova et al. | |
| 6,172,067 B1 | 1/2001 | Ito et al. | |
| 6,180,643 B1 | 1/2001 | Zablocki et al. | |
| 6,221,637 B1 | 4/2001 | Hida et al. | |

(Continued)

FOREIGN PATENT DOCUMENTS

| | | |
|---|---|---|
| DE | 43 29 309 A1 | 3/1995 |
| EP | 0 079 164 A1 | 5/1983 |

(Continued)

OTHER PUBLICATIONS

CAS Registry No. 1350531-79-1, disclosed by Jackson, et al.; title: Process for the preparation of substituted nicotinic acid esters, Quick View; From PCT Int. Appl. (2004), WO 2004078729 A1 Sep. 16, 2004. (Year: 2004).*
Unknown author, title: surfactants, the essential chemical industry published by UNiversity of York, Mar. 18, 2013 (Year: 2013).*
Acevedo et al., "Molecular Weight of Petroleum Asphaltenes: A Comparison between Mass Spectrometry and Vapor Pressure Osmometry", Energy & Fuels, 2005, pp. 1548-1560, vol. 19, No. 4.
Annett et al., Necrotic enteritis: Effect of barley, wheat and corn diets on proliferation of Clostridium perfringens type A, Avian Pathology, 2002, pp. 599-602, vol. 31.

(Continued)

*Primary Examiner* — Yanzhi Zhang

(74) *Attorney, Agent, or Firm* — Polsinelli PC

(57) ABSTRACT

The present invention relates to microemulsions and methods of preparing and using the microemulsions.

14 Claims, 5 Drawing Sheets

(56) References Cited

U.S. PATENT DOCUMENTS

| | | | |
|---|---|---|---|
| 6,310,095 B1 | 10/2001 | Sebti et al. |
| 6,358,978 B1 | 3/2002 | Ritzeler et al. |
| 6,518,243 B1 | 2/2003 | Kahne et al. |
| 6,727,285 B1 | 4/2004 | Haik, Jr. |
| 6,939,693 B2 | 9/2005 | Lorbert et al. |
| 6,949,498 B2 | 9/2005 | Murphy et al. |
| RE39,403 E | 11/2006 | Robert et al. |
| 7,250,443 B2 | 7/2007 | Desai et al. |
| 7,316,996 B2 | 1/2008 | Muhlradt et al. |
| 7,381,416 B2 | 6/2008 | Erdelmeir et al. |
| 7,714,077 B2 | 5/2010 | Tanaka et al. |
| 7,989,532 B2 | 8/2011 | Li et al. |
| 8,053,194 B2 | 11/2011 | Shinya et al. |
| 8,084,551 B2 | 12/2011 | Ara et al. |
| 8,158,731 B2 | 4/2012 | Stefanisin et al. |
| 9,169,203 B2 | 10/2015 | Grady et al. |
| 9,284,294 B2 | 3/2016 | Arhancet et al. |
| 9,801,845 B2 | 10/2017 | Arhancet et al. |
| 2002/0077306 A1 | 6/2002 | Dinkelborg et al. |
| 2002/0193596 A1 | 12/2002 | Sebti et al. |
| 2003/0143366 A1 | 7/2003 | Foley |
| 2004/0175434 A1 | 9/2004 | Schasteen et al. |
| 2006/0134061 A1 | 6/2006 | Muhlradt et al. |
| 2007/0053866 A1 | 3/2007 | Abou-Nemeh |
| 2007/0208105 A1 | 9/2007 | Grossman |
| 2008/0019860 A1 | 1/2008 | Abou-Nemeh et al. |
| 2008/0241223 A1 | 10/2008 | Nivaggioli et al. |
| 2009/0200511 A1 | 8/2009 | Allen et al. |
| 2010/0048586 A1 | 2/2010 | Deigin |
| 2010/0098801 A1 | 4/2010 | Kobler et al. |
| 2010/0252433 A1 | 10/2010 | Dratz et al. |
| 2011/0070188 A1 | 3/2011 | Fowers et al. |
| 2011/0262492 A1 | 10/2011 | Messersmith et al. |
| 2011/0295006 A1 | 12/2011 | Kobler et al. |
| 2012/0128616 A1 | 5/2012 | Voisin et al. |
| 2012/0283364 A1 | 11/2012 | Sarazin et al. |
| 2013/0178540 A1 | 7/2013 | Grady et al. |
| 2013/0209391 A1 | 8/2013 | Arhancet et al. |
| 2013/0209392 A1 | 8/2013 | Arhancet et al. |
| 2014/0011930 A1 | 1/2014 | Buono et al. |
| 2016/0326349 A1 | 11/2016 | Arhancet et al. |
| 2016/0340302 A1 | 11/2016 | Arhancet et al. |
| 2017/0002295 A1 | 1/2017 | Arhancet et al. |

FOREIGN PATENT DOCUMENTS

| | | |
|---|---|---|
| EP | 0 186 977 A2 | 7/1986 |
| EP | 0 322 633 A1 | 7/1989 |
| EP | 0 572 271 A2 | 12/1993 |
| EP | 0 576 949 A1 | 1/1994 |
| EP | 2 082 739 A1 | 7/2009 |
| GB | 1 219 649 A | 1/1971 |
| JP | 06-316557 | 11/1994 |
| JP | H07-291922 A | 11/1995 |
| JP | 2004001190 A | 1/2004 |
| JP | 2005232047 A | 9/2005 |
| JP | 2008239601 A | 10/2008 |
| WO | 92/15547 A1 | 9/1992 |
| WO | 93/00908 A1 | 1/1993 |
| WO | 95/06484 A1 | 3/1995 |
| WO | 95/09142 A1 | 4/1995 |
| WO | 95/34535 A1 | 12/1995 |
| WO | 96/36314 A2 | 11/1996 |
| WO | 98/12156 A1 | 3/1998 |
| WO | 98/32735 A1 | 7/1998 |
| WO | 98/51260 A2 | 11/1998 |
| WO | 99/04647 A1 | 2/1999 |
| WO | 00/61537 A2 | 10/2000 |
| WO | 01/42333 A2 | 6/2001 |
| WO | 01/49273 A2 | 7/2001 |
| WO | 03/010157 A1 | 2/2003 |
| WO | 03/082836 A1 | 10/2003 |
| WO | 03/106615 A2 | 12/2003 |
| WO | 2005/011738 A2 | 2/2005 |
| WO | 2005/042546 A2 | 5/2005 |
| WO | 2005/077882 A1 | 8/2005 |
| WO | 2005/113582 A1 | 12/2005 |
| WO | 2006/019149 A1 | 2/2006 |
| WO | 2006/052775 A2 | 5/2006 |
| WO | 2006/057868 A1 | 6/2006 |
| WO | 2007/030012 A2 | 3/2007 |
| WO | 2007/092847 A2 | 8/2007 |
| WO | 2007/136703 A1 | 11/2007 |
| WO | 2007/144411 A1 | 12/2007 |
| WO | 2008/006076 A2 | 1/2008 |
| WO | 2008/114505 A1 | 9/2008 |
| WO | 2009/005871 A2 | 1/2009 |
| WO | 2009/055054 A2 | 4/2009 |
| WO | 2009/055653 A1 | 4/2009 |
| WO | 2009/088879 A1 | 7/2009 |
| WO | 2009/127009 A1 | 10/2009 |
| WO | 2009/137465 A2 | 11/2009 |
| WO | 2010/012712 A1 | 2/2010 |
| WO | 2010/013138 A2 | 2/2010 |
| WO | 2010/033223 A1 | 3/2010 |
| WO | 2010/048586 A1 | 4/2010 |
| WO | 2010/082175 A2 | 7/2010 |
| WO | 2010/100390 A1 | 9/2010 |
| WO | 2010/126794 A1 | 11/2010 |
| WO | 2010/128303 A1 | 11/2010 |
| WO | 2011/008985 A2 | 1/2011 |
| WO | 2011/028007 A2 | 3/2011 |
| WO | 2011/046946 A2 | 4/2011 |
| WO | 2011/064384 A1 | 6/2011 |
| WO | 2011/084466 A1 | 7/2011 |
| WO | 2011/084620 A2 | 7/2011 |
| WO | 2011/085058 A1 | 7/2011 |
| WO | 2011/119759 A1 | 9/2011 |
| WO | 2012/006475 A1 | 1/2012 |
| WO | 2012/095481 A1 | 7/2012 |
| WO | 2013/059107 A1 | 4/2013 |
| WO | 2013/103598 A2 | 7/2013 |
| WO | 2013/119955 A1 | 8/2013 |
| WO | 2013/119959 A1 | 8/2013 |
| WO | 2013/150058 A1 | 10/2013 |
| WO | 2015/100225 A1 | 7/2015 |
| WO | 2016/179489 A1 | 11/2016 |
| WO | 2017/004161 A1 | 1/2017 |

OTHER PUBLICATIONS

Blanco et al., "A comparative study of the physicochemical properties of perfluorinated and hydrogenated amphiphiles", Journal of Colloid and Interface Science, 2005, pp. 247-260, vol. 288.

Buchwald et al., "Quantitative Structure—Metabolism Relationships: Steric and Nonsteric Effects in the Enzymatic Hydrolysis of Noncongener Carboxylic Esters", Journal of Medicinal Chemistry, 1999, pp. 5160-5168, vol. 42, No. 25.

Dahanayake et al., "Relationship of Structure to Properties of Surfactants. 13. Surface and Thermodynamic Properties of Some Oxyethylenated Sulfates and Sulfonates", The Journal of Physical Chemistry, 1986, pp. 2413-2418, vol. 90, No. 11.

Dorwald, "Side Reactions in Organic Synthesis", Wiley-VCH Verlag GmbH & Co. KGaA, Weinheim, 2005, Preface, p. IX.

Ge et al., "Crystallographic studies on the binding of selectively deuterated LLD- and LLL-substrate epimers by isopenicillin N synthase", Biochemical and Biophysical Research Communications, 2010, pp. 659-664, vol. 398, No. 4.

Glukhareva et al., "Krafft Points of Some Mixtures Based on Individual Sodium Soaps", Colloid Journal, 1995, pp. 253-255, vol. 57, No. 2.

Guzman et al., "Molecular Weight Determination of Asphaltenes from Colombian Crudes by Size Exclusion Chromatography (SEC) and Vapor Pressure Osmometry (VPO)", Petroleum Science and Technology, 2009, pp. 801-816, vol. 27.

Jackson et al., "Mixtures of Nonionic Surfactants made from Renewable Resources with Alkyl Sulfates and Sodium n-Alkanecarboxylates: Comparison of Mixing Behavior using Rubingh's Treatment", Journal of Surfactants and Detergents, 2013, pp. 893-902, vol. 16.

Kulinski et al., "Plasticization of Poly(L-lactide) with Poly(propylene glycol)", Biomacromolecules, 2006, pp. 2128-2135, vol. 7, No. 7.

(56) References Cited

OTHER PUBLICATIONS

Labrecque et al., "Citrate Esters as Plasticizers for Poly(lactic acid)", Journal of Applied Polymer Science, 1997, pp. 1507-1513, vol. 66.

Lensing et al., "Efficacy of a lactylate on production performance and intestinal health of broilers during a subclinical Clostridium perfringens infection", Poultry Science, 2010, pp. 2401-2409, vol. 89.

Ljunberg et al., "The Effects of Plasticizers on the Dynamic Mechanical and Thermal Properties of Poly(Lactic Acid)", Journal of Applied Polymer Science, 2002, pp. 1227-1234, vol. 86.

Lopez-Rodriguez et al., "Plasticization of Poly-L-lactide with L-Lactide, D-Lactide, and D,L-Lactide Monomers", Polymer Engineering and Science, 2013, pp. 2073-2080, vol. 53.

Moore et al., "Pharmacological Effects of Introducing a Double Bond into a Binding Site of Oxytocin. Analogues with L-3,4-Dehydroproline in Position 7", Journal of Medicinal Chemistry, 1977, pp. 495-500, vol. 20, No. 4.

Murariu et al., "Polylactide (PLA) designed with desired end-use properties: 1. PLA compositions with low molecular weight ester-like plasticizers and related performances", Polymers for Advanced Technologies, 2008, pp. 636-646, vol. 19.

Onisko et al., "Metabolism of Cycloate in Radish Leaf: Metabolite Identification by Packed Capillary Flow Fast Atom Bombardment Tandem Mass Spectrometry", Biological Mass Spectrometry, 1994, pp. 626-636, vol. 23.

Onisko et al., "Identification of Fonofos Metabolites in Latuca sativa, Beta vulgaris, and Triticum aestivum by Packed Capillary Flow Fast Atom Bombardment Tandem Mass Spectrometry", Journal of Agricultural and Food Chemistry, 2002, pp. 1922-1928, vol. 50, No. 7.

Stellner et al., "Hardness Tolerance of Anionic Surfactant Solutions. 1. Anionic Surfactant with Added Monovalent Electrolyte", Langmuir, 1989, pp. 70-77, vol. 5, No. 1.

Bentley et al., "Action of nitrogen trichloride on certain proteins. II. Synthesis of methionine sulphoximine and other sulphoximines", Research Association of British Flour-Millers, Cereals Research Station, St Albans, 1950, pp. 265-272.

Brenner et al., "Isolation of enzymatically manufactured L-methionyl-L-methionine and L-methionyl-L-methionyl-L-methionine: a comparison with synthetic products", Helv. Chim. Acta, 1951, pp. 2085-2096, vol. 34. (German language document; no translation available).

Bueno et al., "1,4-Dioxane-2,5-dione-type monomers derived from L-ascorbic and D-isoascorbic acids. Synthesis and polymerisation", Carbohydrate Research, 2009, pp. 2100-2104, vol. 344.

Chen et al., "ProSAR: A New Methodology for Combinatorial Library Design", J. Chem. Inf. Model., 2009, pp. 603-614, vol. 49, No. 3.

Cohen-Arazi et al., "Preparation of New α-Hydroxy Acids Derived from Amino Acids and Their Corresponding Polyesters", Macromolecules, 2008, pp. 7259-7263, vol. 41, No. 20, and Supporting Information.

Dechy-Cabaret et al., "Controlled Ring-Opening Polymerization of Lactide and Glycolide", Chemical Reviews, 2004, pp. 6147-6176, vol. 104, No. 12.

Franz et al., "Synthesis of Functional Polydepsipeptides via Direct Ring-Opening Polymerization and Post-Polymerization Modification", Macromolecular Chemistry and Physics, 2010, pp. 809-820, vol. 211.

Gerhardt et al., "Functional Lactide Monomers: Methodology and Polymerization", Biomacromolecules, 2006, pp. 1735-1742, vol. 7, No. 6.

Gu et al., "Synthesis and evaluation of a biodegradable material with cell recognition motives", Carbohydrate Polymers, 2008, pp. 572-578, vol. 74.

Hayashi et al., "Analysis of Amide Bond Formation with an α-Hydroxy-β-amino Acid Derivative, 3-Amino-2-hydroxy-4-phenylbutanoic Acid, as an Acyl Component: Byproduction of Homobislactone", Journal of Organic Chemistry, 2001, pp. 5537-5544, vol. 66, No. 16.

Huthmacher, "Polyhydroxymethionine", Biopolymers, 2003, pp. 81-87, vol. 9.

Jiang et al., "Clickable" Polyglycolides: Tunable Synthons for Thermoresponsive, Degradable Polymers, Macromolecules, 2008, pp. 1937-1944, vol. 41, No. 6.

Jing et al., "Cyclohexyl-Substituted Polyglycolides with High Glass Transition Temperatures", Macromolecules, 2007, pp. 9304-9312, vol. 40, No. 26.

Jost et al., "Papain Catalyzed Oligomerization of α-Amino Acids. Synthesis and Characterization of Water-Insoluble Oligomers of L-Methionine", Helvetica Chimica Acta, 1980, pp. 375-384, vol. 63.

Kasai et al., "Correlation between Molecular Weight Distribution of Oligo-L-methionine Prepared by Papain-catalyzed Polymerization and Its Supplementary Effect in a Low Protein Diet", Biosci. Biotech. Biochem., 1992, pp. 1884-1885, vol. 56, No. 11.

Koban et al., "Kinetics of Hydrolysis of Dimeric and Trimeric Methionine Hydroxy Analogue Free Acid under Physiological Conditions of pH and Temperature", J. Agric. Food Chem., 1984, pp. 393-396, vol. 32, No. 2.

Kolitz et al., "Biodegradable Polyesters Derived from Amino Acids", Macromolecules, 2009, pp. 4520-4530, vol. 42, No. 13.

Lee et al., "Papain Catalyzed Polymerization of L-α-Amino Acid Methyl Esters with Hydrophobic Side Chains", Chemistry Express, 1990, pp. 741-744, vol. 5, No. 10.

Leemhuis et al., "Synthesis and characterization of allyl functionalized poly(α-hydroxy)acids and their further dihydroxylation and epoxidation", European Polymer Journal, 2008, pp. 308-317, vol. 44.

Nguyen et al., "Polydepsipeptides: Investigation of Secondary Structure", American Chemical Society Division of Polymeric Materials: Science and Engineering Fall 2009, pp. 798-799, vol. 2 of 2, PMSE Preprints vol. 101, Fall 2009, Washington D.C., USA, Aug. 16-20, 2009.

Ouchi et al., "Preparation of Poly(L-lactide)-Based Microspheres Having a Cationic or Anionic Surface Using Biodegradable Surfactants", Biomacromolecules, 2002, pp. 885-888, vol. 3, No. 5.

Ouchi et al., "Design of Lactide-Based Copolymers for Biomaterials", Polymer Preprints, Division of Polymer Chemistry, Inc., American Chemical Society, Fall 2002, pp. 648-649, vol. 43, No. 2.

Ouchi et al., "Synthesis of a block copolymer of L-lactide and depsipeptide with pendant thiol groups", Designed Monomers and Polymers, 2000, pp. 279-287, vol. 3, No. 3.

Pounder et al., Synthesis and Organocatalytic Ring-Opening Polymerization of Cyclic Esters Derived from L-Malic Acid, Biomacromolecules, 2010, pp. 1930-1939, vol. 11, No. 8.

Qi et al., "Cytotoxicity and Cellular Uptake Evaluation of Mitoxantrone-Loaded Poly(lactic acid-co-lysine) Arginine-Glycine-Aspartic Acid Nanoparticles", Journal of Applied Polymer Science, 2010, pp. 1011-1015, vol. 119.

Rajesh et al., "Enzymatic Synthesis and Characterization of L-Methionine and 2-Hydroxy-4-(methylthio)butanoic Acid (HMB) Co-oligomers", Journal of Agricultural and Food Chemistry, 2003, pp. 2461-2467, vol. 51, No. 9.

Reynal et al., "Omasal Flow of Soluble Proteins, Peptides, and Free Amino Acids in Dairy Cows Fed Diets Supplemented with Proteins of Varying Ruminal Degradabilities", Journal of Dairy Science, 2007, pp. 1887-1903, vol. 90, No. 4.

Ristic et al., "The Properties of Poly(L-Lactide) Prepared by Different Synthesis Procedure", Journal of Polymers and the Environment, 2011, pp. 419-430, vol. 19.

Rubinshtein et al., "Facile Procedure for Generating Side Chain Functionalized Poly(α-hydroxy acid) Copolymers from Aldehydes via a Versatile Passerini-Type Condensation", Organic Letters, 2010, pp. 3560-3563, vol. 12, No. 15.

Williams, "Synthesis of functionalized biodegradable polyesters", Chem. Soc. Rev., 2007, pp. 1573-1580, vol. 36.

Yan et al., "Synthesis and RGD peptide modification of poly{(lactic acid)-co-[(glycolic acid)-alt-(L-lysine)]}", e-Polymers, 2008, pp. 1-12, No. 028.

(56) References Cited

OTHER PUBLICATIONS

Yin et al., "Synthesis and Characterization of Substituted Polylactides", American Chemical Society, Polymer Preprints 1998, pp. 158-159, vol. 39, No. 2.
Yin et al., "Preparation and Characterization of Substituted Polylactides", Macromolecules, 1999, pp. 7711-7718, vol. 32, No. 23.
Yu et al., "Synthesis of 3-Benzyl-Glyceric Acid: A Key Intermediate of a Novel Cyclic Ester Monomer", Chinese Journa of Polymer Science, 2002, pp. 177-180, vol. 20, No. 2.
Braunova et al., "Hydrolytically and Reductively Degradable High-Molecular-Weight Poly(ethylene glycol)s", Macromolecular Chemistry and Physics, 2007, pp. 2642-2653, vol. 208.
Crich et al., "Amino Acid and Peptide Synthesis and Functionalization by the Reaction of Thioacids with 2,4-Dinitrobenzenesulfonamides", Organic Letters, 2007, pp. 4423-4426, vol. 9, No. 22.
Hamachi et al., "Anisotropic Incorporation of Lipid-Anchored Myoglobin into a Phospholipid Bilayer Membrane", Journal of the American Chemical Society, 1993, pp. 4966-4970, vol. 115, No. 12.
Hooks et al., "Development of Homomultimers and Heteromultimers of Lung Cancer-Specific Peptoids", Biopolymers, 2011, pp. 567-577, vol. 96, No. 5.
Itoh et al., "Design, Synthesis, Structure—Selectivity Relationship, and Effect on Human Cancer Cells of a Novel Series of Histone Deacetylase 6-Selective Inhibitors", Journal of Medicinal Chemistry, 2007, pp. 5425-5438, vol. 50, No. 22.
Joullie et al., "Evolution of amide bond formation", ARKIVOC, 2010 (viii), pp. 189-250.
Katritzky et al., "Convenient and Efficient Preparation of N-Protected (α-Aminoacyl)oxy-Substituted Terpenes and Alkanes", Synthesis: Journal of Synthetic Organic Chemistry, 2006, pp. 4135-4142, No. 24.
Landis et al., "Solid-phase synthesis of chiral 3,4-diazaphospholanes and their application to catalytic asymmetric allylic alkylation", PNAS, 2004, pp. 5428-5432, vol. 101, No. 15.
Liu et al., "Chemistry of Periodate-Mediated Cross-Linking of 3,4-Dihydroxylphenylalanine-Containing Molecules to Proteins", Journal of the American Chemical Society, 2006, pp. 15228-15235, vol. 128, No. 47.
Liu et al., "Synthesis and Insecticidal Activities of Novel Spin-Labeled Derivatives of Camptothecin", Heteroatom Chemistry, 2011, pp. 687-691, vol. 22, No. 6.
Montalbetti et al., "Amide bond formation and peptide coupling", Tetrahedron, 2005, pp. 10827-10852, vol. 61.
Rahman et al., "Conformation and biological studies of synthesized Trp4-Met5 enkephalin N-protected with 3,5-dimethoxy-α, α-dimethylbenzoylcarbonyl group", Die Pharmazie, 1988, pp. 116-117, vol. 43.
Rahman et al., "Relationship Between Conformation and Physicochemical Properties of Polypeptides. I. Synthesis of Homo- and Co-Oligopeptides by the Liquid-Phase Method", Biopolymers, 1980, pp. 173-187, vol. 19.
Ribeiro et al., "H-NMR Studies of Polyoxyethylene-Bound Homo-oligo-L-methionines", Biopolymers, 1982, pp. 2225-2239, vol. 21.
Valeur et al., "Amide bond formation: beyond the myth of coupling reagents", Chemical Society Reviews, 2009, pp. 606-631, vol. 38.
Abell et al., "Synthesis of a [1,4]dioxane-2,5-dione based-peptidomimetic scaffold", ARKIVOC, 2006 (iii), pp. 72-76.
Acosta, "The HLD-NAC equation of state for microemulsions formulated with nonionic alcohol ethoxylate and alkylphenol ethoxylate surfactants", Colloids and Surfaces A: Physicochemical and Engineering Aspects, 2008, pp. 193-204, vol. 320.
Acosta et al., "The Characteristic Curvature of Ionic Surfactants", Journal of Surfactants and Detergents, 2008, pp. 145-158, vol. 11.
Balg et al., "Inhibition of Helicobacter pylori Aminoacyl-tRNA Amidotransferase by Puromycin Analogues", Journal of the American Chemical Society, 2008, pp. 3264-3265, vol. 130, No. 11.
Bourrel et al., "A Correlation for Phase Behavior of Nonionic Surfactants", Journal of Colloid and Interface Science, 1980, pp. 451-461, vol. 75, No. 2.
Bouton et al., "A QSPR Model for the Prediction of the "Fish-Tail" Temperature of CiE4/Water/Polar Hydrocarbon Oil Systems", Langmuir, 2010, pp. 7962-7970, vol. 26, No. 11.
CAS No. 1306322-34-8, Entered in STN Jun. 6, 2011; p. 1.
Clint et al., "Thermodynamics of Micellization of Homologous Series of n-Alkyl Methyl Sulphoxides and n-Alkyl (dimethyl)phospine Oxides", Journal of the American Chemical Society, Faraday Transactions 1, 1975, pp. 946-954, vol. 71.
Clint, "Micellization of Mixed Nonionic Surface Active Agents", Journal of the American Chemical Society, Faraday Transactions 1, 1975, pp. 1327-1334, vol. 71.
Evans et al., "Nanomolar-Affinity, Non-Peptide Oxytocin Receptor Antagonists", Journal of Medicinal Chemistry, 1993, pp. 3993-4005, vol. 36, No. 25.
Hansen, "The Three Dimensional Solubility Parameter and Solvent Diffusion Coefficient, Their Importance in Surface Coating Formulation", PhD Thesis, Copenhagen Danish Technical Press, 1967; 103 pgs.
Hennaux et al., "Novel nonionic polymerisable surfactants based on sulfoxides. 1. Monomer synthesis and general surfactant behaviour", Colloid Polym. Sci., 2001, pp. 1149-1159, vol. 279.
Hennaux et al., "Novel nonionic surfactants based on sulfoxides. 2. Homo- and copolymers", Colloid Polym. Sci., 2003, pp. 807-814, vol. 281.
Huh, "Interfacial Tensions and Solubilizing Ability of a Microemulsion Phase That Coexists with Oil and Brine", Journal of Colloid and Interface Science, 1979, pp. 408-426, vol. 71, No. 2.
Ignasiak et al., "Characterization by mass spectrometry and IRMPD spectroscopy of the sulfoxide group in oxidized methionine and related compounds", Chemical Physics Letters, 2011, pp. 29-36, vol. 502.
In't Veld et al., "Synthesis of biodegradable polyesteramides with pendant functional groups", Makromolekulare Chemie, Macromolecular Chemistry and Physics, 1992, pp. 2713-2730, vol. 193, No. 11.
John et al., "Synthesis and Modification of New Biodegradable Copolymers: Serine/Glycolic acid Based Copolymers", New Biodegradable Copolymers, 1997, pp. 1901-1907.
Kim et al., "Reduction-Sensitive Self-Aggregates as a Novel Delivery System", Macromolecular Chemistry and Physics, 2010, pp. 956-961, vol. 211.
Komori et al., "Structure Activity Relationships of Synthetic Antibiotic Analogues of Chryscandin", The Journal of Antibiotics, 1985, pp. 1182-1203, vol. 38, No. 9.
Leemhuis et al., "A Versatile Route to Functionalized Dilactones as Monomers for the Synthesis of Poly(α-hydroxy) Acids", Eur. J. Org. Chem., 2003, pp. 3344-3349.
Li et al., "High Throughput Synthesis of Peptide α-Thioesters Through the Use of "Volatilizable" Support", Journal of Combinatorial Chemistry, 2008, pp. 613-616, vol. 10, No. 5 (and Supporting Information).
Marquez et al., "Partitioning of Ethoxylated Alkylphenol Surfactants in Microemulsion-Oil-Water Systems: Influence of Physiocochemical Formulation Variables", Langmuir, 2002, pp. 6021-6024, vol. 18, No. 16.
Maryanoff et al., "Macrocyclic Peptide Inhibitors of Serine Proteases. Convergent Total Synthesis of Cyclotheonamides A and B via a Late-Stage Primary Amine Intermediate. Study of Thrombin Inhibition under Diverse Conditions", Journal of the American Chemical Society, 1995, pp. 1225-1239, vol. 117, No. 4.
Noga et al., "Synthesis and Modification of Functional Poly(lactide) Copolymers: Toward Biofunctional Materials", Biomacromolecules, 2008, pp. 2056-2062, vol. 9, No. 7.
Queste et al., "The EACN scale for oil classification revisited thanks to fish diagrams", Journal of Colloid and Interface Science, 2007, pp. 98-107, vol. 312.
Ramli et al., "Efficient Manual Fmoc Solid-Phase Synthesis of the N-Terminal Segment of Surfactant Protein B (SP-B1-25)", Protein & Peptide Letters, 2009, pp. 810-814, vol. 16, No. 7.
Roenne et al., "Lipase-Catalyzed Esterification of Lactic Acid with Straight-Chain Alcohols", Journal of the American Oil Chemists' Society, 2005, pp. 881-885, vol. 82, No. 12.

(56) References Cited

OTHER PUBLICATIONS

Salager et al., "Optimum Formulation of Surfactant/Water/Oil Systems for Minimum Interfacial Tension or Phase Behavior", Society of Petroleum Engineers Journal, 1979, pp. 107-115, vol. 19.
Salager et al., "Partitioning of Ethoxylated Octylphenol Surfactants in Microemulsion-Oil-Water Systems: Influence of Temperature and Relation between Partitioning Coefficient and Physicochemical Formulation", Langmuir, 2000, pp. 5534-5539, vol. 16, No. 13.
Sato et al., "Oxidation of sulfides to sulfoxides and sulfones with 30% hydrogen peroxide under organic solvent-and halogen-free conditions", Tetrahedron, 2001, pp. 2469-2476, vol. 57.
Shinoda et al., "The Correlation between Phase Inversion Temperature in Emulsion and Cloud Point in Solution of Nonionic Emulsifier", The Journal of Physical Chemistry, 1964, pp. 3485-3490, vol. 68, No. 12.
Sottmann et al., "Ultralow interfacial tensions in water-n-alkane-surfactant systems", The Journal of Chemical Physics, 1997, pp. 8606-8615, vol. 106, No. 20.
Vaccaro et al., "Colloidal particles composed of amphiphilic molecules binding gadolinium complexes and peptides as tumor-specific contrast agents in MRI: physico-chemical characterization", Soft Matter, The Royal Society of Chemistry, 2009, pp. 2504-2512, vol. 5.
van Weerden et al., "Utilization of the polymers of methionine hydroxy analogue free acid (MHA-FA) in broiler chicks", Archly Fuer Gefluegelkunde, 1992, pp. 63-68, vol. 56, No. 2.
Weissbach et al., "Peptide Methionine Sulfoxide Reductase: Structure, Mechanism of Action, and Biological Function", Archives of Biochemistry and Biophysics, 2002, pp. 172-178, vol. 397, No. 2.
Yoshiizumi et al., "Studies on Scavenger Receptor Inhibitors. Part 1: Synthesis and Structure—Activity Relationships of Novel Derivatives of Sulfatides", Bioorganic & Medicinal Chemistry, 2002, pp. 2445-2460, vol. 10.
Yu et al., "Synthesis and characterization of arginine-glycine-aspartic peptides conjugated poly(lactic acid-co-L-lysine) diblock copolymer", Journal of Materials Science: Materials in Medicine, 2008, pp. 1275-1281, vol. 19, No. 3.
Paul, Uses and applications of microemulsions, Current Science, Apr. 25, 2001, vol. 80, No. 8, pp. 990-1001.

* cited by examiner

SURFACTANT MICROEMULSIONS

FIELD

The present disclosure relates to microemulsions and methods of preparing and using the microemulsions.

BACKGROUND

Surfactants, or surface active agents, are compounds that lower the surface tension of a liquid, the interfacial tension between two liquids, or the interfacial tension between a liquid and a solid. Most surfactants can be formulated into microemulsions, which are microheterogeneous, thermodynamically stable mixtures of oil, water, and surfactant. Microemulsions are useful in a variety of applications including enhanced oil recovery, as well as various industrial and consumer cleaning formulations. Because of the many uses of microemulsions, there is a need for microemulsions that have extremely low oil-water interfacial tensions.

SUMMARY

One aspect of the present disclosure encompasses a microemulsion. The microemulsion comprises at least one surfactant comprising a sulfoxide ester moiety of Formula (I), an oil phase, and an aqueous phase. The sulfoxide ester moiety of Formula (I) having the following structure:

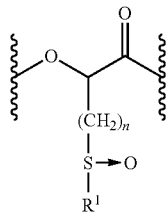

(I)

wherein $R^1$ is alkyl, substituted alkyl, alkenyl, substituted alkenyl, aryl, or substituted aryl; and n is an integer from 1 to 20.

Another aspect of the present disclosure encompasses a process for preparing the microemulsion. The process comprises homogenizing (i) at least one surfactant comprising a sulfoxide ester moiety of Formula (I), (ii) an oil phase, and (iii) an aqueous phase.

An additional aspect of the present disclosure encompasses a method of cleaning an article. The process comprises contacting the article with a microemulsion comprising at least one surfactant comprising a sulfoxide ester moiety of Formula (I):

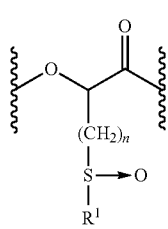

(I)

wherein $R^1$ is alkyl, substituted alkyl, alkenyl, substituted alkenyl, alkynyl, substituted alkynyl, aryl, or substituted aryl; and n is an integer from 1 to 20.

DETAILED DESCRIPTION

Figure 1:
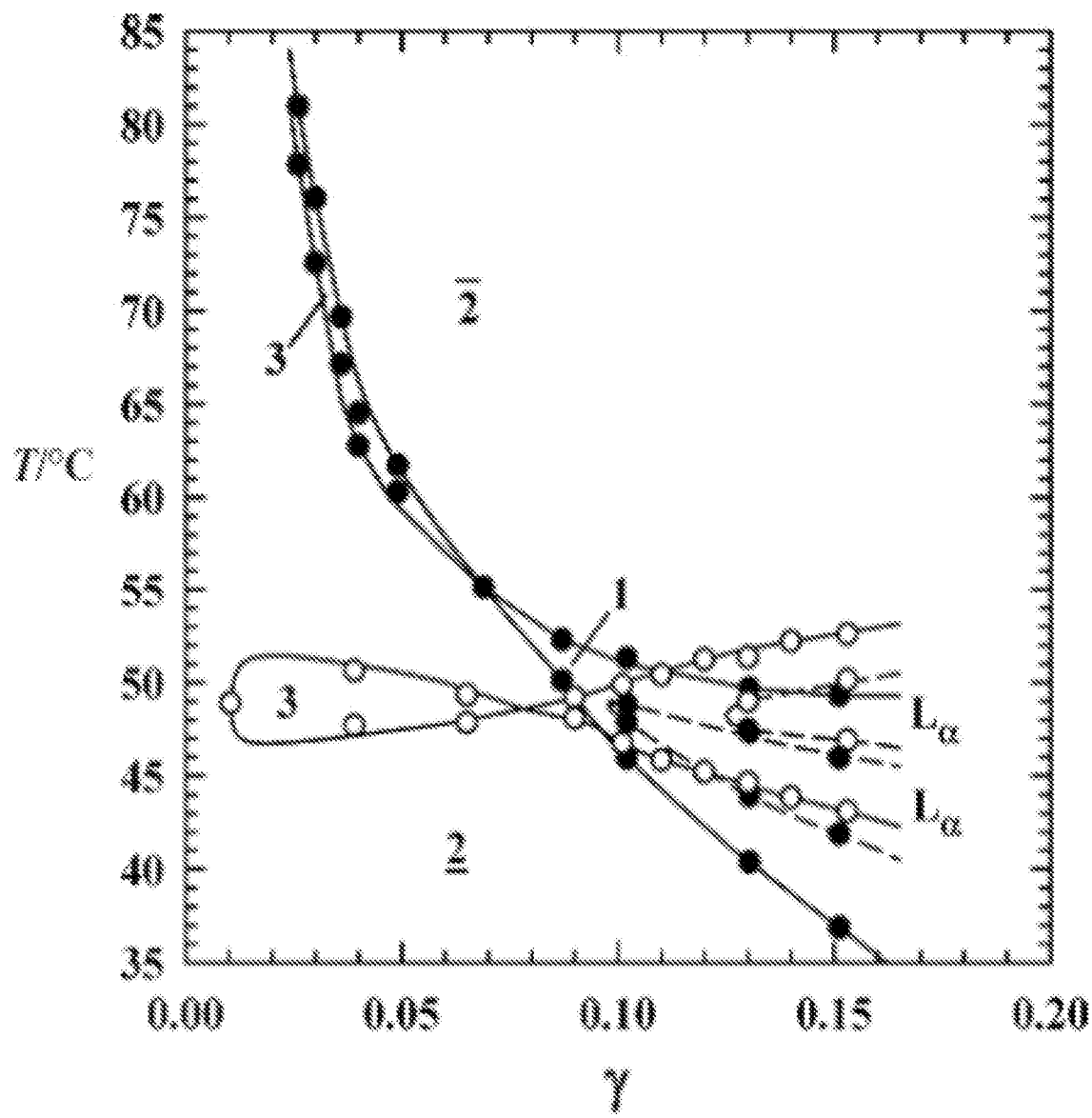
FIG. 1 depicts a phase or "Fish" diagram of nonionic surfactants versus n-octane systems.

Provided herein are microemulsions, methods of making, and methods of using the microemulsions. The microemulsion comprises at least one surfactant, an oil phase, and an aqueous phase. The one or more surfactants in the microemulsion comprise a sulfoxide ester moiety of Formula (I). The microemulsions disclosed herein have a key property; namely, they have very low interfacial tensions. The inventors have discovered that the temperature at which a microemulsion is formed can be controlled by the identity and amount of the at least one sulfoxide ester moiety-containing surfactant.

(I) Microemulsion

One aspect of the present disclosure encompasses a microemulsion. The microemulsion comprises at least one surfactant comprising a sulfoxide ester moiety, an oil phase, and an aqueous phase.

Each of the components of the microemulsion is detailed below.

(a) Surfactant

The microemulsion comprises at least one surfactant. In general, the surfactant comprises a sulfoxide ester moiety of Formula (I):

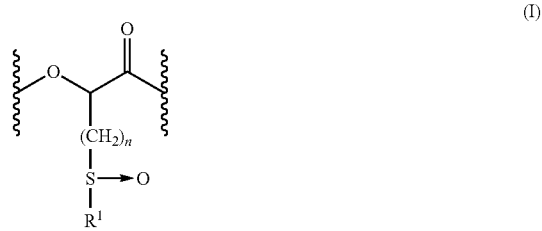

(I)

wherein:

$R^1$ is alkyl, substituted alkyl, alkenyl, substituted alkenyl, alkynyl, substituted alkynyl, aryl, or substituted aryl; and n is an integer from 1 to 20.

In some embodiments, the surfactant comprising the sulfoxide ester moiety of Formula (I) may be a compound of Formula (II):

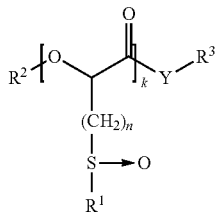

(II)

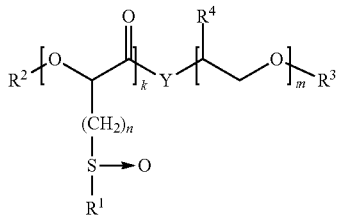

(III)

wherein:

$R^1$ is alkyl, substituted alkyl, alkenyl, substituted alkenyl, alkynyl, substituted alkynyl, aryl, or substituted aryl;

$R^2$ is hydrogen, alkyl, substituted alkyl, alkenyl, or substituted alkenyl;

$R^3$ is alkyl or alkenyl having 6 or more carbon atoms;

Y is O or NH;

k is an integer from 1 to 500; and n is an integer from 1 to 20.

In some embodiments, $R^1$ is alkyl, substituted alkyl, alkenyl, substituted alkenyl, alkynyl, substituted alkynyl, aryl, or substituted aryl. In various embodiments, $R^1$ may be $C_1$ to $C_{10}$ alkyl or $C_1$ to $C_6$ alkyl, with the alkyl being linear, branched, or cyclic. In some embodiments, $R^1$ may be methyl, ethyl, propyl, isopropyl, butyl, tert-butyl, hexyl, cyclohexyl, and the like. In specific embodiments, $R^1$ may be methyl. Additionally, $R^1$ in each repeat unit may differ.

In certain embodiments, $R^2$ may be hydrogen, alkyl, substituted alkyl, alkenyl, substituted alkenyl, aryl, or substituted aryl. In some embodiments, $R^2$ may be hydrogen, $C_1$ to $C_{10}$ alkyl, phenyl, substituted phenyl, or benzyl. In specific embodiments, $R^2$ may be hydrogen or $C_1$ to $C_6$ alkyl.

In general, $R^3$ is an alkyl or alkenyl chain having 6 or more carbon atoms, wherein the alkyl or alkenyl may be linear or branched. For example, $R^3$ may comprise up to 500 carbons atoms. In various embodiments, $R^3$ may range from $C_6$ to $C_{500}$, from $C_6$ to $C_{400}$, from $C_6$ to $C_{300}$, from $C_6$ to $C_{200}$, from $C_6$ to $C_{100}$, from $C_6$ to $C_{50}$, or from $C_6$ to $C_{36}$. In certain embodiments, $R^3$ may range from $C_6$ to $C_{30}$. In other embodiments, $R^3$ may range from $C_8$ to $C_{22}$. For example, $R^3$ may be $C_8$, $C_9$, $C_{10}$, $C_{12}$, $C_{14}$, $C_{16}$, $C_{18}$, $C_{20}$, or $C_{22}$.

In some embodiments, Y may be O. In other embodiments, Y may be NH.

In some embodiments, k may range from 1 to 500. In some embodiments, k may range from 1 to 500, 1 to 400, 1 to 300, 1 to 200, 1 to 100, 1 to 90, 1 to 80, 1 to 70, 1 to 60, 1 to 50, 1 to 40, 1 to 30, 1 to 20, or 1 to 10. In other embodiments, k may be 1, 2, 3, 4, 5, 6, 7, 8, 9, or 10.

In general, n may range from 1 to 20 or from 1 to 10. In some embodiments, n may range from 1 to 6. In specific embodiments, n may be 1, 2, 3, or 4.

In some embodiments, $R^1$ may be $C_1$ to $C_{10}$ alkyl, $R^2$ may be hydrogen or $C_1$ to $C_{10}$ alkyl, $R^3$ may be $C_6$ to $C_{36}$, n may be 1 to 10, and k may be 1 to 300. In specific embodiments, $R^1$ may be methyl; $R^2$ may be hydrogen; $R^3$ may be $C_6$ to $C_{30}$, Y may be O or NH; n may be 2; and k may be from 1 to 10.

In some embodiments, the surfactant comprising the sulfoxide ester moiety of Formula (I) may be a compound of Formula (III):

wherein:

$R^1$ is alkyl, substituted alkyl, alkenyl, substituted alkenyl, alkynyl, substituted alkynyl, aryl, or substituted aryl;

$R^2$ is hydrogen, alkyl, substituted alkyl, alkenyl, or substituted alkenyl;

$R^3$ is alkyl or alkenyl having 3 or more carbon atoms;

$R^4$ is hydrogen or alkyl;

Y is O or NH;

k is an integer from 1 to 500;

n is an integer from 1 to 20; and m is an integer from 1 to 50.

In various embodiments, $R^1$ may be alkyl, alkenyl, alkynyl, aryl, substituted alkyl, substituted alkenyl, substituted alkynyl, or substituted aryl. Additionally, $R^1$ in each repeat unit may differ. In exemplary embodiments, $R^1$ may be $C_1$ to $C_{10}$ alkyl, with the alkyl being linear, branched, or cyclic. In specific embodiments, $R^1$ may be methyl, ethyl, propyl, isopropyl, butyl, tert-butyl, hexyl, cyclohexyl, and the like. In exemplary embodiments, $R^1$ is methyl.

In certain embodiments, $R^2$ may be hydrogen, alkyl, substituted alkyl, alkenyl, substituted alkenyl, aryl, or substituted aryl. In specific embodiments, $R^2$ may be hydrogen or $C_1$ to $C_6$ alkyl.

In general, $R^3$ is an alkyl or alkenyl chain having 3 or more carbon atoms, wherein the alkyl or alkenyl may be linear or branched. For example, $R^3$ may comprise up to 500 carbons atoms. In various embodiments, $R^3$ may range from $C_3$ to $C_{500}$, from $C_3$ to $C_{400}$, from $C_3$ to $C_{300}$, from $C_3$ to $C_{200}$, from $C_3$ to $C_{100}$, from $C_3$ to $C_{50}$, or from $C_3$ to $C_{36}$. In certain embodiments, $R^3$ may range from $C_6$ to $C_{30}$. In other embodiments, $R^3$ may range from $C_8$ to $C_{22}$. For example, $R^3$ may be $C_8$, $C_9$, $C_{10}$, $C_{12}$, $C_{14}$, $C_{16}$, $C_{18}$, $C_{20}$, or $C_{22}$.

In various embodiments, $R^3$ may be $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, or $C_{36}$ alkyl or alkenyl, wherein the alkyl or alkenyl may be linear or branched. In certain embodiments, $R^3$ may range from $C_6$ to $C_{30}$. In other embodiments, $R^3$ may range from $C_8$ to $C_{22}$. For example, $R^3$ may be $C_8$, $C_9$, $C_{10}$, $C_{12}$, $C_{14}$, $C_{16}$, $C_{18}$, $C_{20}$, or $C_{22}$.

In certain embodiments, $R^4$ may be hydrogen or $C_1$ to $C_{10}$ alkyl, with the alkyl being linear or branched. In some embodiments, $R^4$ may be methyl or ethyl. In exemplary embodiments, $R^4$ is hydrogen.

In some embodiments, Y is O. In other embodiments, Y is NH.

In some embodiments, k may range from 1 to 500. In some embodiments, k may range from 1 to 500, 1 to 400, 1 to 300, 1 to 200, 1 to 100, 1 to 90, 1 to 80, 1 to 70, 1 to 60, 1 to 50, 1 to 40, 1 to 30, 1 to 20, or 1 to 10. In other embodiments, k may be 1, 2, 3, 4, 5, 6, 7, 8, 9, or 10.

In general, n may range from 1 to 20 or from 1 to 10. In some embodiments, n may range from 1 to 6. In specific embodiments, n may be 1, 2, 3, or 4.

In some embodiments, m may range from 1 to 30. In some specific embodiments, m may be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In specific embodiments, $R^1$ may be methyl; $R^2$ may be hydrogen; $R^4$ may be hydrogen; Y may be O or NH; n may be 2; k may be 1, 2, or 3; m may range from 1 to 10; and $R^3$ may be $C_8$, $C_9$, $C_{10}$, $C_{12}$, $C_{14}$, $C_{16}$, or $C_{18}$. In other specific embodiments, $R^1$ may be methyl; $R^2$ may be hydrogen; $R^4$ may be hydrogen; Y may be O or NH; n may be 2; k may be 1 or 2; m may range from 10 to 20; and $R^3$ may be $C_8$, $C_9$, $C_{10}$, $C_{12}$, $C_{14}$, $C_{16}$, or $C_{18}$.

In some embodiments, the surfactant comprising the sulfoxide moiety of Formula (I) may be a compound of Formula (IV):

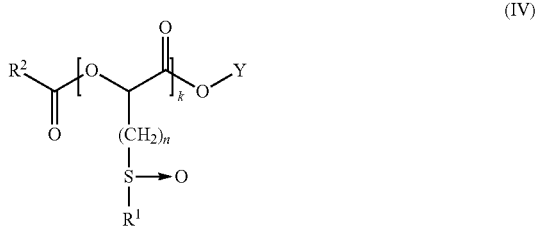

(IV)

wherein:
$R^1$ is alkyl, substituted alkyl, alkenyl, substituted alkenyl, alkynyl, substituted alkynyl, aryl, or substituted aryl;
$R^2$ is hydrogen, alkyl, substituted alkyl, alkenyl, or substituted alkenyl;
Y is a cation chosen from hydrogen, ammonium, an alkali metal, an alkaline earth metal, or a transition metal;
k is an integer from 1 to 500; and
n is an integer from 1 20.

In various embodiments, $R^1$ may be unsubstituted or substituted alkyl, alkenyl, or aryl. In some embodiments, $R^1$ may be $C_1$ to $C_6$ alkyl or $C_1$ to $C_6$ alkenyl, wherein alkyl and alkenyl may be linear, branched, or cyclic. In certain embodiments, $R^1$ may be methyl, ethyl, propyl, isopropyl, butyl, tert-butyl, hexyl, cyclohexyl, and the like. In specific embodiments, $R^1$ may be methyl.

In certain embodiments, $R^2$ may be $C_{10}$ to $C_{30}$ alkyl, substituted $C_{10}$ to $C_{30}$ alkyl, $C_8$ to $C_{30}$ alkenyl, or substituted $C_8$ to $C_{30}$ alkenyl. The alkyl and alkenyl groups may be linear, branched, or cyclic, and the alkenyl groups may contain from one to six carbon-carbon double bonds. In some embodiments, $R^2$ may be $C_{10}$ to $C_{24}$ alkyl or $C_{10}$ to $C_{24}$ alkenyl. In specific embodiments, $R^2$ may be $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl or alkenyl.

In some embodiments, k may range from 1 to 500. In some embodiments, k may range from 1 to 500, 1 to 400, 1 to 300, 1 to 200, 1 to 100, 1 to 90, 1 to 80, 1 to 70, 1 to 60, 1 to 50, 1 to 40, 1 to 30, 1 to 20, or 1 to 10. In other embodiments, k may be 1, 2, 3, 4, 5, 6, 7, 8, 9, or 10.

In some embodiments, n may be an integer from 1 to 20, from 1 to 10, or from 1 to 6. In certain embodiments, n may be 1, 2, 3, or 4. In specific embodiments, n may be 2.

In some embodiments, Y may be hydrogen. In other embodiments, Y may be ammonium, an alkali metal, an alkaline earth metal, or a transition metal.

In some embodiments, the surfactant comprising the sulfoxide moiety of Formula (I) may be a compound of Formula (IVa):

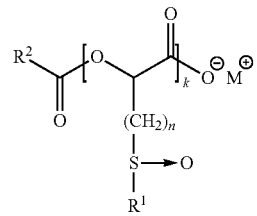

(IVa)

wherein:
$R^1$ is alkyl, substituted alkyl, alkenyl, substituted alkenyl, alkynyl, substituted alkynyl, aryl, or substituted aryl;
$R^2$ is hydrogen, alkyl, substituted alkyl, alkenyl, or substituted alkenyl;
k is an integer from 1 to 500; and
M is a cation chosen from ammonium, an alkali metal, an alkaline earth metal, or a transition metal.

Suitable metals include sodium, potassium, lithium, cesium, magnesium, calcium, manganese, cobalt, nickel, copper, zinc, and iron. The ratio of the anionic compound to the metal may range from about 1:1 to about 3:1. In specific embodiments, the cation may be sodium or potassium.

In exemplary embodiments, M may be hydrogen, sodium, or potassium, $R^1$ is methyl; $R^2$ is $C_{10}$ to $C_{24}$ alkyl, k is from 1 to 10, and n is 2.

In general, the amount of the surfactant comprising the sulfoxide ester moiety of Formula (I) in the microemulsion may be from about 0.1 wt. % to about 6 wt. %. In some embodiments, the amount of the surfactant comprising the sulfoxide ester moiety of Formula (I) in the microemulsion may be from about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.5 wt. %, about 2 wt. %, about 2.5 wt. %, about 3 wt. %, about 3.5 wt. %, about 4 wt. %, about 4.5 wt. %, about 5 wt. %, about 5.5 wt. %, or about 6 wt. %. In exemplary embodiments, the amount of the surfactant comprising the sulfoxide ester moiety of Formula (I) in the microemulsion may range from about 1 wt. % to about 3 wt. %, or about 5 wt. %.

The sulfoxide ester moieties of Formula (I) disclosed herein generally have at least one chiral center, as denoted with an asterisk in the structure below

(I)

Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, and so forth.

(b) Oil Phase

The microemulsion comprises an oil phase. In some embodiments, the oil phase may comprise one or more oils that can be volatile or non-volatile, and may be, without limit, animal oils, vegetable oils, natural oils, synthetic oils, hydrocarbon oils, silicone oils, semi-synthetic derivatives thereof, and combinations thereof. In other embodiments, the oil phase may comprise at least one hydrocarbon solvent.

Suitable oils include, without limit, mineral oil, squalene oil, flavor oils, silicon oil, essential oils, water insoluble vitamins, isopropyl stearate, butyl stearate, octyl palmitate, cetyl palmitate, tridecyl behenate, diisopropyl adipate, dioctyl sebacate, menthyl anthranhilate, cetyl octanoate, octyl salicylate, isopropyl myristate, neopentyl glycol dicarpate cetols, CERAPHYLS, decyl oleate, diisopropyl adipate, $C_{12}$-$C_{15}$ alkyl lactates, cetyl lactate, lauryl lactate, isostearyl neopentanoate, myristyl lactate, isocetyl stearoyl stearate, octyldodecyl stearoyl stearate, hydrocarbon oils, isoparaffin, fluid paraffins, isododecane, petrolatum, argan oil, canola oil, chile oil, coconut oil, corn oil, cottonseed oil, flaxseed oil, grape seed oil, mustard oil, olive oil, palm oil, palm kernel oil, peanut oil, pine seed oil, poppy seed oil, pumpkin seed oil, rice bran oil, safflower oil, tea oil, truffle oil, vegetable oil, apricot (kernel) oil, jojoba oil (*Simmondsia chinensis* seed oil), grapeseed oil, macadamia oil, wheat germ oil, almond oil, rapeseed oil, gourd oil, soybean oil, sesame oil, hazelnut oil, maize oil, sunflower oil, hemp oil, bois oil, kuki nut oil, avocado oil, walnut oil, fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, marhoram flower oil, orange flower oil, rose flower oil, ylang-ylang flower oil, bark oil, *cassia* bark oil, cinnamon bark oil, *sassafras* bark oil, wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, oleic acid, linoleic acid, oleyl alcohol, isostearyl alcohol, semi-synthetic derivatives thereof, and any combinations thereof.

In some embodiments, the oil may be a volatile oil. The volatile oil may be the organic solvent, or the volatile oil can be present in addition to an organic solvent. Suitable volatile oils include, without limit, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, *chenopodium* oil, citronellal, citral, citronellol, chamazulene, yarrow, guaiazulene, chamomile, semi-synthetic derivatives, or combinations thereof.

Suitable hydrocarbon solvents include, without limit, alkanes (e.g., hexane, n-hexane, heptane, n-heptane, octane, n-octane, nonane, n-nonane, decane, n-decane, etc.), cycloalkanes (e.g., cyclopentane, cyclohexane, cycloheptane, cyclooctane, etc.), and substituted cycloalkanes (e.g., methyl cyclohexane, ethyl cyclohexane, propyl cyclohexane, etc.). In an exemplary embodiment, the at least one hydrocarbon solvent may comprise cyclohexane, methyl cyclohexane, ethyl cyclohexane, propyl cyclohexane, and combinations thereof. In another exemplary embodiment, the at least one hydrocarbon solvent may comprise hexane, heptane, octane, nonane, decane, or combinations thereof.

In some embodiments, the at least one hydrocarbon solvent may have an equivalent alkane carbon number (EACN) of from about −15 to about 25. In other embodiments, the at least one hydrocarbon solvent may have an equivalent alkane carbon number (EACN) of about −15, about −14.5, about −14, about −13.5, about −13, about −12.5, about −11, about −10.5 about −10, about −9.5, about −9, about −8.5 about −8, about −7.5, about −7, about −6.5 about −6, about −5.5, about −5, about −4.5 about −4, about −3.5, about −3, about −2.5 about −2, about −1.5, about −1, about −0.5, about 0, about 0.5, about 1, about 1.5, about 2, about 2.5, about 3, about 3.5 about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16.5, about 17, about 17.5, about 18, about 18.6, about 19, about 19.5, about 20, about 20.5, about 21, about 21.5, about 22, about 22.5, about 23, about 23.5, about 24, about 24.5, or about 25.

In some embodiments, the amount of the oil phase in the microemulsion can and will vary depending on the identity of the oil phase. In some embodiments, the amount of the oil phase in the microemulsion may be from about 1% (v/v) to about 99% (v/v). In other embodiments, the amount of the oil phase in the microemulsion may be from about 1% (v/v), about 5% (v/v), about 10% (v/v), about 15% (v/v), about 20% (v/v), about 25% (v/v), about 30% (v/v), about 35% (v/v), about 40% (v/v), about 45% (v/v), about 50% (v/v), about 55% (v/v), about 60% (v/v), about 65% (v/v), about 70% (v/v), about 75% (v/v), about 80% (v/v), about 85% (v/v), about 90% (v/v), about 95% (v/v), or about 99% (v/v).

(c) Aqueous Phase

The microemulsion comprises an aqueous phase. In general, the aqueous phase may comprise any type of aqueous liquids.

Suitable aqueous liquids include, without limit, distilled water, purified water, de-ionized water, tap water, and solutions (e.g., salt solutions). In exemplary embodiments, the aqueous liquid may be de-ionized water.

In some embodiments, the aqueous liquid may be a salt solution. Suitable salts may include, without limit, alkali metal salts and alkaline earth metal salts. Suitable metals include sodium, potassium, lithium, cesium, magnesium, calcium, manganese, cobalt, copper, zinc, and iron. The salts maybe halide salts, nitrite salts, nitrate salts, sulfide salts, and the like. In exemplary embodiments, the salt may be sodium chloride or potassium chloride.

In some embodiments, the amount of salt in the aqueous liquid may be from about 0.1 wt. % to about 20 wt. %. In some embodiments, the amount of salt in the aqueous liquid may be from about 0.1 wt. % to about 20 wt. %, from about 0.5 wt. % to about 15 wt. %, or from about 1 wt. % to about 15 wt. %. In other embodiments, the amount of salt in the aqueous liquid may be about 1 wt. %, 1.5 wt. %, about 2 wt. %, about 2.5 wt. %, about 3 wt. %, about 3.5 wt. %, about 4 wt. %, about 4.5 wt. %, about 5 wt. %, about 5.5 wt. %, about 6 wt. %, about 6.5 wt. %, about 7 wt. %, about 7.5 wt. %, about 8 wt. %, about 8.5 wt. %, about 9 wt. %, about 9.5 wt. %, about 10 wt. %, about 10.5 wt. %, about 11 wt. %, about 11.5 wt. %, about 12 wt. %, about 12.5 wt. %, about 13 wt. %, about 13.5 wt. %, about 14 wt. %, about 14.5 wt. %, about 15 wt. %, about 15.5 wt. %, about 16 wt. %, about 16.5 wt. %, about 17 wt. %, about 17.5 wt. %, about 18 wt. %, about 18.5 wt. %, about 19 wt. %, about 19.5 wt. %, or about 20 wt. %.

In some embodiments, the amount of the aqueous phase in the microemulsion can and will vary depending on the identity of the aqueous phase. In some embodiments, the amount of the aqueous phase in the microemulsion may be from about 1% (v/v) to about 99% (v/v). In other embodiments, the amount of the aqueous phase in the microemulsion may be from about 1% (v/v), about 5% (v/v), about 10% (v/v), about 15% (v/v), about 20% (v/v), about 25% (v/v), about 30% (v/v), about 35% (v/v), about 40% (v/v), about 45% (v/v), about 50% (v/v), about 55% (v/v), about 60% (v/v), about 65% (v/v), about 70% (v/v), about 75% (v/v), about 80% (v/v), about 85% (v/v), about 90% (v/v), about 95% (v/v), or about 99% (v/v).

(d) Physical Properties of the Microemulsion

In some embodiments, the microemulsion may have a interfacial tension ($IFT_{min}$) value of from about $6\times10^{-4}$ (mN/m) to about $10\times10^{-2}$ (mN/m). In other embodiments, the microemulsion may have a interfacial tension ($IFT_{min}$) value of about $6\times10^{-4}$ (mN/m), about $6.5\times10^{-4}$ (mN/m), about $7\times10^{-4}$ (mN/m), about $7.5\times10^{-4}$ (mN/m), about $8\times10^{-4}$ (mN/m), about $8.5\times10^{-4}$ (mN/m), about $9\times10^{-4}$ (mN/m), about $9.5\times10^{-4}$ (mN/m), about $1\times10^{-3}$ (mN/m), about $1.5\times10^{-3}$ (mN/m), about $2\times10^{-3}$ (mN/m), about $2.5\times10^{-3}$ (mN/m), about $3\times10^{-3}$ (mN/m), about $3.5\times10^{-3}$ (mN/m), about $4\times10^{-3}$ (mN/m), $4.5\times10^{-3}$ (mN/m), about $5\times10^{-3}$ (mN/m), about $5.5\times10^{-3}$ (mN/m), about $6\times10^{-3}$ (mN/m), about $6.5\times10^{-3}$ (mN/m), about $7\times10^{-3}$ (mN/m), about $7.5\times10^{-3}$ (mN/m), about $8\times10^{-3}$ (mN/m), about $8.5\times10^{-3}$ (mN/m), about $9\times10^{-3}$ (mN/m), about $9.5\times10^{-3}$ (mN/m), or about $10\times10^{-2}$ (mN/m).

In some embodiments, the microemulsion may be a Type I oil/water emulsion, a Type II water/oil emulsion, a Type III bicontinuous emulsion, or a Type IV single phase, stable water/oil mixture.

(II) Compositions

An additional aspect of the present disclosure encompasses a composition. The composition comprises a microemulsion as defined in Section (I) and optionally an additional component.

Each of the components of the composition are detailed below.

(a) Emulsion

In general, the compositions disclosed herein comprising a microemulsion as defined in Section (I).

In general, the amount of the microemulsion in the composition may range from about 0.1% to about 99.9% of the total weight of the composition. In various embodiments, the amount of the microemulsion in the composition may range from about 0.1% to about 1%, from about 1% to about 3%, from about 3% to about 10%, from about 10% to about 30%, or from about 30% to about 99.9% of the total weight of the composition.

(b) Additional Components

The composition may further comprise at least one agent chosen from surfactant, pH regulating agents, stain-removing enzymes, other types of surfactants, optical brightening agents, bleaching agents, thickening agents, scale inhibitors, chelating agents, water softening agents, foam control agents, dispersants, hydrotropes, linkers, fillers, disintegrants, preservatives, coloring agents, fragrance agents, or combinations thereof.

The composition may comprise another surfactant in addition to the sulfoxide ester moiety containing surfactant. Suitable additional surfactants include, without limit, anionic surfactants, cationic surfactants, and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Cationic surfactants include alkyl trimethyl quaternary ammonium salts, alkyl dimethyl benzyl quaternary ammonium salts, dialkyl dimethyl quaternary ammonium salts, and imidazolinium salts. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkyl polyethylene glycol esters and diesters. Also included are betaines and sultanas, amphoteric surfactants such as alkyl amphoacetates and amphodiacetates, alkyl amphopropripionates and amphodipropionates, and alkyliminodiproprionate.

In some embodiments, the composition may comprise at least one pH regulating agent. Suitable pH regulating agents include, without limit, organic carboxylic acids (e.g., acetic acid, ascorbic acid, citric acid, formic acid, glycolic acid, gluconic acid, lactic acid, malic acid, maleic acid, propionic acid, succinic acid, tartaric acid, etc.) or salts thereof other acids (e.g., hydrochloric acid, boric acid, nitric acid, phosphoric acid, sulfuric acid, etc.), alkali metal or ammonium carbonates, bicarbonates, hydroxides, phosphates, nitrates, and silicates; organic bases (such as, for example, pyridine, triethylamine (i.e., monoethanol amine), diisopropylethylamine, N methylmorpholine, N,N dimethylaminopyridine); and combinations of any of the above.

In other embodiments, the composition may comprise at least one stain-removing enzyme. Suitable enzymes include, without limit, proteases, peptidases, subtilisin, mannanases, amylases, carbohydrases, and lipases.

In further embodiments, the composition may comprise at least one optical brightener. Optical brighteners (also known as optical brightening agents, fluorescent brightening agents, or fluorescent whitening agents) are dyes that absorb light in the ultraviolet and violet region and reemit light in the blue regions. Suitable optical brightening agents include, without limit, triazine-stilbenes, coumarins, imidazolines, diazoles, triazoles, benzoxazolines, and biphenyl-stilbenes. In one embodiment, the optical brightening agent may be a sulfonated tetrabenzotetraazaaporphine derivative. In some embodiments, the optical brightening agent may be used in combination with a polyol, such as polyethylene glycol, polypropylene glycol, or polyvinyl alcohol.

In still other embodiments, the composition may comprise at least one bleaching agent. Suitable bleaching agents include, without limit, hydrogen peroxide, peroxy acid, sodium perborate, sodium percarbonate, sodium hypochlorite, and sodium dichloroisocyanurate.

In some embodiments, the composition may comprise at least one thickening agent (or theological additive). Suitable thickening agents include, without limit, cellulosic ethers (such as hydroxycellulose, hydroxypropyl cellulose, hydroxymethylpropyl cellulose, hydroxyethyl cellulose, carboxymethyl cellulose, methylhydroxyethyl cellulose), polyvinylpyrrolidone, poly(vinylpyridine-N-oxide), bentonites, starches, gums, and combinations thereof.

In certain embodiments, the composition may comprise at least one scale inhibitor. Suitable scale inhibitors include, without limit, phosphonates, sodium hexametaphosphate, sodium tripolyphosphate, oxalic acid, phosphoric acid, sulfamic acid, and carboxymethyl inulin.

In other embodiments, the composition may comprise at least one chelating agent. Suitable chelating agents include, without limit, EDTA, DTPA, HEDP, HEDTA, NTA, HEIDA, PBTC, phosphonates, carboxymethyl inulin, trisodium phosphate, sodium hexametaphosphate, sodium tripolyphosphate, tetrasodium pyrophosphate, potassium tripolyphosphate, tetrapotassium pyrophosphate, citric acid, gluconic acid, sodium gluconate, DTPMP, and combinations thereof.

In further embodiments, the composition may comprise at least one water softening agent. Suitable water softening agents include, without limit, sodium triphosphate, sodium tripolyphosphate, sodium carbonate, sodium silicate, zeolites, and citric acid.

In some embodiments, the composition may comprise at least one foam control agent, such as ethylene oxide/propylene oxide copolymers or silicone.

In still other embodiments, the composition may comprise at least one dispersant. Suitable dispersants include, without limit, phosphonates, carboxymethyl inulin, sodium hexametaphosphate, sodium tripolyphosphate, tetrasodium pyrophosphate, potassium tripolyphosphate, acrylic polymers, and combinations thereof.

In other embodiments, the composition may comprise at least one hydrotrope. Hydrotropes are compounds that improve the solubility of surfactants in aqueous solutions. Suitable hydrotropes include, without limit, sodium toluenesulfonate, potassium toluene sulfonate, sodium xylene sulfonate, potassium xylene sulfonate, ammonium xylene sulfonate, sodium cumene sulfonate, ammonium cumene sulfonate, alkyl glucoside, complex coco imino glycinate, complex coco imino dipropionate, octyl imino dipropionate, phosphate ester potassium salt, and quaternary fatty methyl amine ethoxylate.

In yet alternate embodiments, the composition may comprise at least one linker. Linkers are amphiphiles that are used to increase surfactant-water interactions (i.e., hydrophilic linkers) or surfactant-oil interactions (i.e., lipophilic linkers). Suitable hydrophilic linkers include without limit alkyl naphthalene sulfonates such as mono- or di-methyl naphthalene sulfonate and diisopropyl naphthalene sulfonate. Suitable lipophilic linkers include, without limit, hydrocarbyl alcohols having 8 or more carbon atoms in the principal chain or their low ethoxylated derivatives.

In other embodiments, the composition may comprise at least one filler. Suitable fillers include, without limit, cellulose, methylcellulose, carboxymethylcellulose, microcrystalline cellulose, calcium sulfate, calcium carbonate, magnesium carbonate, dibasic calcium phosphate, magnesium carbonate, magnesium oxide, calcium silicate, sodium chloride, talc, modified starches, lactose, sucrose, mannitol, sorbitol, and combinations thereof.

In still other embodiments, the composition may comprise at least one disintegrant. Suitable disintegrants include, without limit, starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pectin, and tragacanth, and combinations thereof.

In other embodiments, the composition may comprise at least one a preservative. Suitable preservatives include, without limit, antioxidants, such as alpha-tocopherol or ascorbate, and antimicrobials, such as parabens, chlorobutanol, phenol, glutaraldehyde, benzoic acid, quaternary ammonium salts, bronopol, hydrogen peroxide, sodium dichloroisocyanurate, sodium hypochlorite, and combinations thereof.

In still other embodiments, the composition may comprise at least one coloring agent. Suitable coloring agents include, but are not limited to, food, drug and cosmetic colors (FD&C), drug and cosmetic colors (D&C), external drug and cosmetic colors (Ext. D&C), and other dyes known in the industry.

In further embodiments, the composition may comprise at least one fragrance (or perfume) agent. Suitable fragrance (or perfume) agents are well known in the art.

The weight fraction of the optional additional agents in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In various embodiments, the composition may be a liquid solution, an aqueous solution, an emulsion, a gel, a paste, a powder, a granular mixture, a pelleted mixture, or a solid.

(III) Methods of Making

Another aspect of the present invention encompasses a method of preparing a microemulsion. The microemulsion comprises at least one surfactant as detailed in Section (I)(a), an oil phase as detailed in Section (I)(b), and an aqueous phase as detailed in Section (I)(c).

In some embodiments, the at least one surfactant, the oil phase, and the aqueous phase are combined to form a homogenous dispersion. In some embodiments, the at least one surfactant, the oil phase, and the aqueous phase are combined to make a microemulsion. In some embodiments, the microemulsion is formed via comminution or condensation techniques.

Suitable comminution techniques include, without limit, a stirred tank reactor, screw loop reactor, turbine-type stirrer, colloidal mill, rotorstator, homogenizer, ultrasound, cavitation, or shaking. In an exemplary embodiment, the emulsion may be formed via shaking.

In general, condensation techniques do not require mechanical energy. Suitable condensation techniques include, without limit, gentle stirring, spontaneous, or swelling.

In some embodiments, the emulsion may be formed at room temperature or at an elevated temperature. In an exemplary embodiment, the emulsion may be formed at room temperature.

In some embodiments, the emulsion may be formed in about 1 day to about 5 days. In some embodiments, the emulsion may be formed in about 1 day, about 1.5 days, about 2 days, about 2.5 days, about 3 days, about 3.5 days, about 4 days, about 4.5 days, or about 5 days. In an exemplary embodiment, the emulsion may be formed in about 3 days.

(IV) Methods of Use

A further aspect of the disclosure provides methods of using the microemulsions as described in Section (I) or the compositions described in Section (II). In some embodiments, the microemulsions or compositions may be used as detergents or emulsifying agents in household or industrial laundry products, hard surface cleaning products, and other types of cleaning products. In other embodiments, the microemulsions or compositions may be used as cleaning agents in health and personal care products or cosmetic products. In still other embodiments, the microemulsions or compositions may be used as surfactants, emulsifying agents, or lubricants in pet or livestock feed or feed ingredients. In yet other embodiments, the microemulsions or compositions may be used as wetting agents in agricultural applications (e.g., pesticide or herbicide applications), textile industry applications (e.g., dry cleaning applications), or construction applications (e.g., road making operations). In further embodiments, the microemulsions or compositions may be used as foaming agents in ore mining operations, drilling operations, waste treatment applications, or firefighting applications. In yet other embodiments, the microemulsions or compositions may be used as emulsifying agents in petroleum production, oil cleanup procedures, mining operations, and other industries. In still other embodiments, the microemulsions or compositions may be used as demulsifying agents in chemical process industry. In yet further embodiments, the microemulsions or compositions may be used as surfactants in oil recovery, oil drilling or crude oil refining applications, metal processing industries, wood processing industries, or soil remediation.

In specific embodiments, a method for cleaning an article is provided. The method comprises contacting the article with a microemulsion or composition disclosed herein. In some embodiments, the process may further comprise contacting the article with a solvent to remove the microemulsion. Typically, the solvent will be an aqueous solvent such as water.

In certain embodiments, the article may be an inanimate object. Non-limiting examples of suitable inanimate objects include as laundry items such as clothing, uniforms, sheets, towels, and other linens; dishes, flatware, and cookware items; food preparation equipment; hard surfaces such as counters, floors, windows, sinks, and bathroom appliances; hospital and health care items; and industrial items or surfaces. As an example, the surface may be an oil contaminated surface, wherein the process entails removing the oil from the contaminated surface. In other embodiments, the article may be an animate object or a part of an animate object. Examples of suitable animate objects include but are not limited to hair, face, hands, feet, and other body parts.

In some embodiments, the compositions may further comprise at least one agent chosen from pH regulating agents, stain-removing enzymes, other types of surfactants, optical brightening agents, bleaching agents, thickening agents, scale inhibitors, chelating agents, water softening agents, foam control agents, dispersants, hydrotropes, linkers, fillers, disintegrants, preservatives, coloring agents, fragrance agents, or combinations thereof.

The compositions disclosed herein may be used in a variety of applications. In general, the usefulness of the compounds or mixtures of compounds relates to their surfactant qualities. For example the compositions disclosed herein may be used to replace alcohol ethoxylate surfactants in numerous products and/or applications.

In general, the microemulsions or compositions of the invention may be used as detergents, wetting agents, solvents, emulsifiers, foaming agents, or dispersants. In some embodiments, the compounds or mixtures of compounds may be used as detergent compounds in laundry detergents, laundry pre-wash products, spot treatments, fabric softeners, automatic dishwasher detergents, hand dishwashing liquids, household detergents, household cleaners, heavy duty cleaners, solid surface cleaners, degreasers, floor cleaners, floor polishes, upholstery cleaners, auto cleaners, institutional cleaners, laboratory cleaners, detergents for biochemistry/ biotechnology applications, personal care products, hand cleaners, shampoos, hair conditioners, hair styling products, hair coloring products, hair shine products, facial cleaners, body washes, shower gels, bath oils, bar soaps, bubble bath, personal wipes, baby cleaning products, toothpastes, dental gels, cosmetic products, face creams, eye creams, anti-aging creams, serums, sun protecting lotions, body lotions, hand lotions, anti-perspirants, tanning lotions, laxatives, industrial cleaners, industrial surfactants, industrial emulsifiers, industrial degreasers, paints, adhesives, inks, quantum dot coatings, anti-fog agents, ski or snowboard waxes, or oil additives. The compositions listed above may be liquids, gels, foams, emulsions, aerosols, powders, granulates, solids, and so forth.

The amount of the surfactant comprising the sulfoxide ester moiety of Formula (I) disclosed herein included in the various microemulsions or compositions or uses listed above can and will vary depending upon the identity of the surfactant comprising the sulfoxide ester moiety of Formula (I) and the intended use of the composition. In general, the amount of the surfactant comprising the sulfoxide ester moiety of Formula (I) may range from about 0.1% to about 99.9% of the total weight of the composition. In various embodiments, of the surfactant comprising the sulfoxide ester moiety of Formula (I) in a composition may range from about 0.1% to about 1%, from about 1% to about 3%, from about 3% to about 10%, from about 10% to about 30%, or from about 30% to about 99.9%.

In other embodiments, the microemulsions or compositions may be used in a variety of applications including textile processing (e.g., pre-scouring, desizing, and/or finishing applications), wool processing, metal processing (e.g., cutting oils and water-based hydraulic fluids), agricultural applications (e.g., emulsifiable concentrates; soil wetting agents; agrochemical formulations), latex production (e.g., emulsion polymerization), paper processing, paper de-inking, oil harvesting or processing (e.g., hydraulic fracturing ("fracking") fluids, crude oil drilling fluids and demulsifiers, wetting agents, mobilization of oil in oil wells, liquid drag reducing agent in pipelines), oil reclamation processes, and enhanced oil recovery processes.

In some embodiments, the surfactants comprising Formula (I) may be used in an enhanced oil recovery process. In further embodiments, the surfactants comprising Formula (I) may be adding to the flooding fluid and then injected to a subterranean reservoir. In some embodiments, the surfactants comprising Formula (I) may form microemulsions in situ within the subterranean reservoir upon contact with the natural acids in the trapped hydrocarbon fluid (e.g., oil).

In exemplary embodiments, the compounds or mixtures of compounds of the invention may replace alkyphenol ethoxylates in various applications such as in household detergents or industrial detergents. For example, the compounds or mixture of compounds may be included in cleaning compositions or laundry detergents. In another exemplary embodiment, the compounds or mixtures of compounds disclosed herein may be used in industrial processes (e.g., oil harvesting processes, oil reclamation processes, textile processing, metal processing, wool processing, etc.).

The amount of the compound or mixture of compounds used in the various applications can and will vary. In general, the amount of the compound or mixture of compounds used in a specific application will depend upon a variety of factors, including the type of application.

Definitions

When introducing elements of the embodiments described herein, the articles "a," "an," "the," and "said" are intended to mean that there are one or more of the elements. The terms "comprising," "including," and "having" are intended to be inclusive and mean that there may be additional elements other than the listed elements.

The term "alkyl" as used herein describes groups which are preferably lower alkyl containing from two to eight carbon atoms in the principal chain and up to 20 carbon atoms. They may be straight or branched chain or cyclic and include methyl, ethyl, propyl, butyl, hexyl, and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl, or substituted naphthyl.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

A "sulfoxide" refers to a compound containing a "sulfinyl" functional group that is attached to two carbon atoms. The sulfinyl group, as depicted as:

represents:

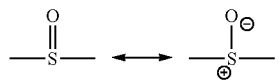

As various changes could be made in the above-described microemulsion, methods of preparing, and methods of use without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All alkanes and alkenes were purchased from Sigma-Aldrich (St. Louis, Mo.) and used without purification. Sodium chloride was purchased from Sigma-Aldrich (St. Louis, Mo.). The DI water used for all experiments was purified via a BARNSTEAD NANOPURE water purification system, with the output water having a resistance of 18MΩ.

The following abbreviations are used herein: DI=deionized water; EACN=equivalent alkane carbon number; EO=ethoxylate; ESO=ester sulfoxide; HLD=hydrophilic-lipophilic difference; IFT=interfacial tensions; and PIT=phase inversion temperature.

The surfactant nomenclature used herein is as follows: $C_n$=length of the alkyl chain; $EO_n$=number of ethoxylate groups; and $ESO_n$=number of ester sulfoxide groups.

Example 1: "Fish" Diagram

A phase or "Fish" diagram of a non-ionic surfactant, hexaethylene glycol monododecyl ether ($C_{12}E_6$) and a technical grade of this same surfactant which is made of a mixture of homologues with different ethylene glycol numbers and hydrophobe lengths (with averages of 6 and 12 respectively) is shown in FIG. 1. With a proper concentration of surfactant, a temperature scan will result in different equilibrium phase behavior of the surfactants-water-oil mixture systems. With increasing temperature, the microemulsions go from oil/water (type I) to bicontinuous (type III) to water/oil (type II), because nonionic surfactants become more and more hydrophobic when hydrogen bonding becomes less important with increased temperature. If the surfactant concentration is too low, the middle phase microemulsion will not be observed even if the optimum temperature is reached. If the surfactant concentration is higher than a certain value, the bicontinuous microemulsion will become a single phase (type IV, thermodynamically stable water/oil mixture). Over an appropriate range of surfactant concentrations, there are two phase inversion temperatures (PITs): one where the phase changes from Type I to Type III and another from Type III to Type II.

Example 2: Phase Inversion Temperature (PIT)

Introduction

The phase inversion temperature is the temperature at which the microemulsion inverts from oil in water (Type I) to water in oil (Type II) or in terms of Equations 1 and 2, HLD goes from being negative to being positive.

$$\text{Ionic HLD}=Cc+\ln(S)-K(\text{EACN})-f(A)-\alpha_T(\Delta T) \quad \text{Equation 1}$$

$$\text{Nonionic HLD}=Cc+b*S-K(\text{EACN})-f(A)+c_T(\Delta T) \quad \text{Equation 2}$$

The reason for this change for EO based surfactants is that the hydrogen bonding between water molecules and ethylene oxide groups of the surfactant becomes less important with increasing temperature which in turn causes the surfactant to effectively become more hydrophobic in water. The PIT phenomena of the nonionic surfactant microemulsions has the same underlying cause as the cloud point phenomena of nonionic surfactant solutions [1].

Methods

For microemulsion preparation, 2 wt % decyl 2-hydroxy-4-(methylsulfinyl) butanoate (hereinafter $C_{10}ESO$) was solubilized in 5 g of cyclohexane, methyl cyclohexane, ethyl cyclohexane, or propyl cyclohexane and mixed with 5 g of DI water or DI water with added sodium chloride (1, 5, and 10 wt %) at a 1:1 weight ratio. For dodecyl 2-hydroxy-4-(methylsulfinyl) (hereinafter $C_{12}ESO$) microemulsions 1 wt % surfactant was used with hexane, heptane, octane, nonane, and decane. Vials at room temperature were shaken intermittently for three days to assure homogenous dispersion.

The samples were then heated to 60° C. and the temperature reduced to 5° C. at 5° C. intervals. Once an approximate PIT was identified, the same procedure was repeated except, the starting temperature was lower than 60° C. and was reduced at 1° C. intervals. If a middle phase only formed at one temperature (narrow range) that temperature was used as the PIT, while if the middle phase formed at more than one temperature (wide range) the temperature corresponding to the maximum coalescence rate was assigned as the PIT. Due to safety issues (flash point of the oils) the temperature never exceeded 60° C.

Results

The PIT results of the sulfoxide surfactants/water/oil systems are presented in Table 1 based on visual measurements. Essentially, these measurements were made by mixing the ingredients and then observing the number and amount of the three phases (from bottom to top: water, bicontinuous phase (if present), oil). The Type I/Type III or Type III/Type II PITs decreases with increasing hydrophobe length and increases with the equivalent alkane carbon number (EACN) of oils. The equivalent alkane carbon number is a number that represents the number of alkane carbons in a system; for normal alkanes it is just the number of carbon atoms; there are different relationships for other carbon moieties such as aromatic carbons, carbonyls etc. The PITs behave similarly to nonionic surfactants in the sense that they are very sensitive to temperature. The PITs of the systems were within the 4° C.-75° C. range, meaning ultralow IFT may be obtained with these surfactants at ambient temperatures.

TABLE 1

PITs of $C_nESOs$ with Various Alkanes

| Surfactant | Alkane (EACN) | PIT (I/III) (° C.) | PIT (III/II) (° C.) |
|---|---|---|---|
| $C_8ESO$ (3%) | Xylenes (1~2) | — | 1 |
| $C_8ESO$ (3%) | Trimethylbezene (2~3) | — | 34 |
| $C_8ESO$ (3%) | Diethylbenzene (2~3) | 25 | 74 |
| $C_8ESO$ (3%) | Cyclohexane (3.5) | 49 | — |
| $C_{10}ESO$ (3%) | Diethylbenzene (2~3) | — | 6 |
| $C_{10}ESO$ (3%) | Cyclohexane (3.5) | 14 | 25 |
| $C_{10}ESO$ (5%) | n-Hexane (6) | 37 | — |
| $C_{10}ESO$ (5%) | n-Heptane (7) | 45 | — |
| $C_{10}ESO$ (3%) | n-Octane (8) | 48 | — |
| $C_{12}ESO$ (1%) | n-Hexane (6) | 14 | 16 |
| $C_{12}ESO$ (1%) | n-Heptane (7) | 18 | 22 |
| $C_{12}ESO$ (1%) | n-Octane (8) | 28 | 31 |
| $C_{12}ESO$ (1%) | n-Nonane (9) | 35 | 36 |
| $C_{12}ESO$ (1%) | n-Decane (10) | 41 | 46 |

Figure 3A:
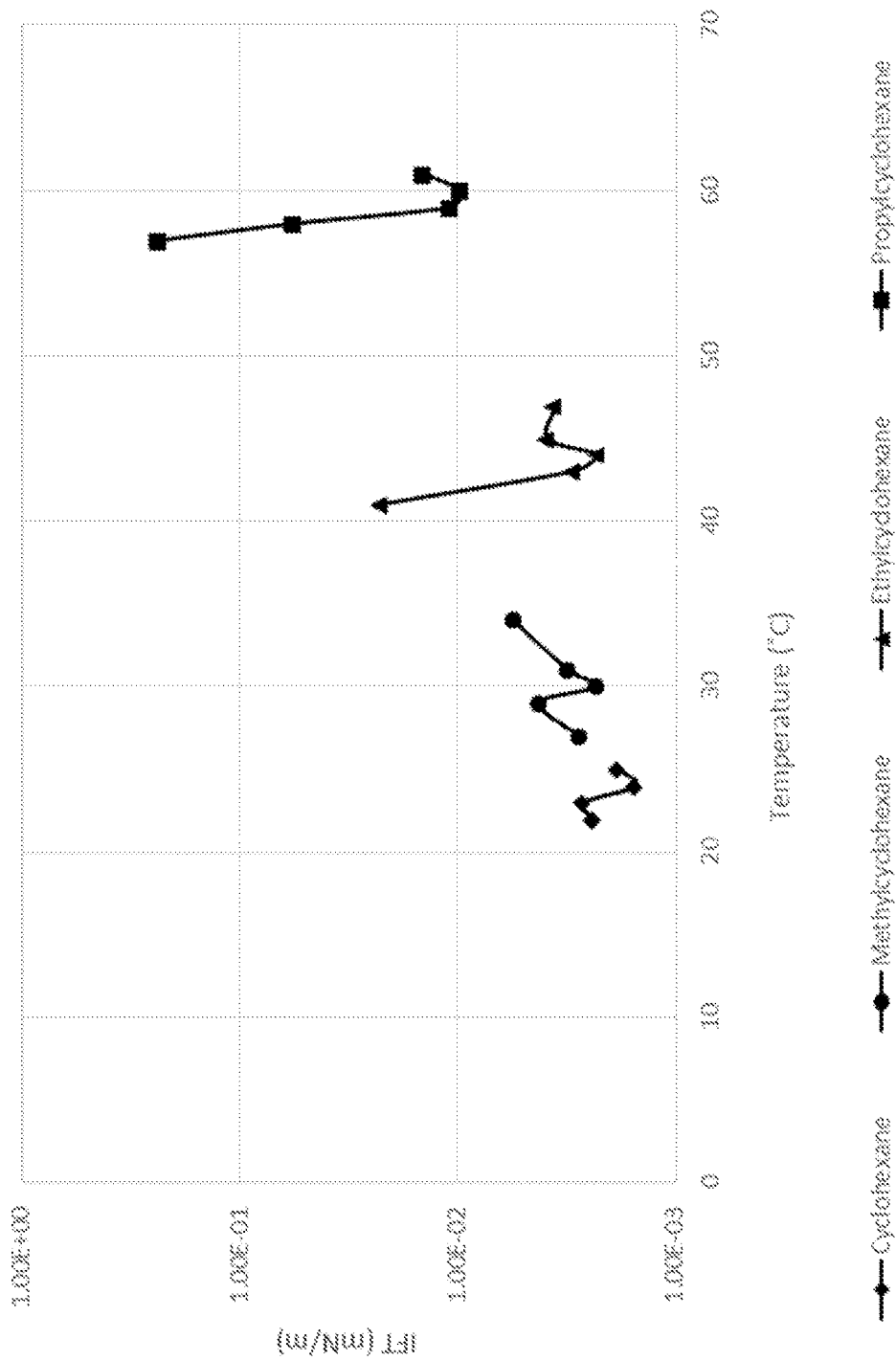
FIG. 3A and FIG. 3B shows IFT (Interfacial Tension) measurements for $C_{10}ESO$ (FIG. 3A) $C_{12}ESO$ (FIG. 3B) and in various hydrocarbons.
Figure 3B:
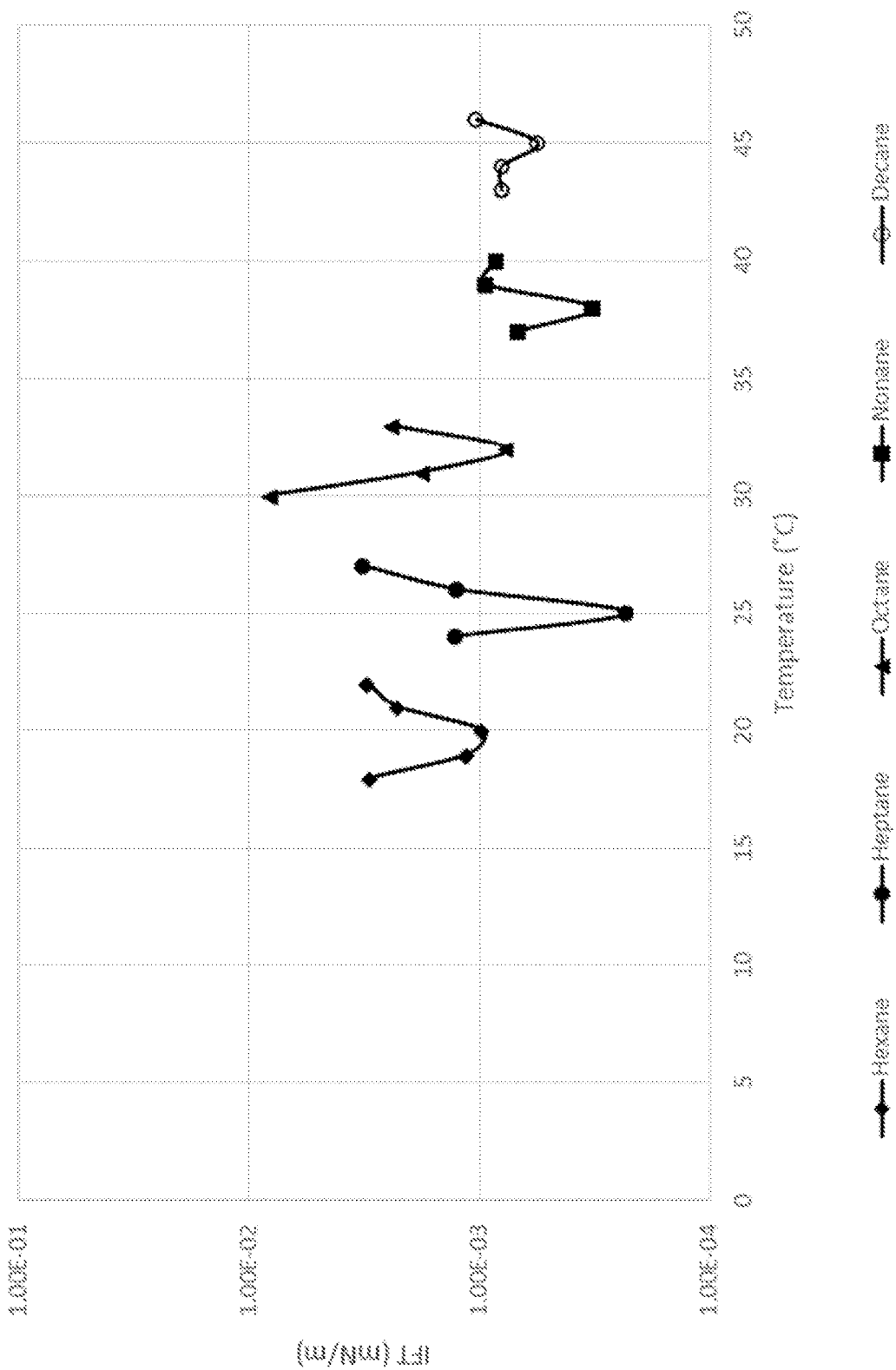

PITs of the sulfoxide surfactants/water/oil systems as well as minimum IFTs are presented in Table 2 and with oil/water IFT vs. temperature curves of $C_{10}ESO/C_{12}ESO$-alkanes presented FIG. 3A and FIG. 3B, respectively. Type III microemulsions were formed with these systems within the temperature range of 0° C.-60° C. IFT of these systems are in the ultralow range (<$10^{-2}$ mN/m), therefore having very high solubilization ratio according to Chun Huh relationship [2]. PITs increase with increasing EACN for both $C_{10}ESO$ and $C_{12}ESO$ microemulsions. Compared to $C_{12}ESO$, $C_{10}ESO$ was able to emulsify oils with lower EACN with a similar PIT ($C_{12}ESO$/n-octane vs. $C_{10}ESO$/methylcyclohexane). An increase of PIT with increasing hydrophobe length and EACN qualitatively agreed with the behaviors of EO-type nonionic surfactants in microemulsions [3-5]. Addition of sodium chloride to the aqueous phase depressed the phase inversion temperature of the emulsions for both surfactants.

TABLE 2

PITs of $C_{10}ESO$ and $C_{12}ESO$ with various oils and various brine concentrations

| Surfactant | Oil | EACN | $IFT_{min}$ (mN/m) | PIT (° C.) Salt Content (wt. %) | | | |
|---|---|---|---|---|---|---|---|
| | | | | 0 | 1 | 5 | 10 |
| $C_{10}ESO$ | Cyclohexane | 2.2[11] | $1.52 \times 10^{-3}$ | 24 | 22 | 18 | 14 |
| $C_{10}ESO$ | Methylcyclohexane | 3.2[12] | $2.29 \times 10^{-3}$ | 30 | 28 | 24 | 15 |
| $C_{10}ESO$ | Ethylcyclohexane | 3.8[13] | $2.26 \times 10^{-3}$ | 44 | 42 | 34 | 28 |
| $C_{10}ESO$ | Propylcyclohexane | 5.6[13] | $9.76 \times 10^{-3}$ | 60 | 60 | 50 | 40 |
| $C_{12}ESO$ | n-Hexane | 6[11] | $9.73 \times 10^{-4}$ | 20 | 18 | 16 | 10 |
| $C_{12}ESO$ | n-Heptane | 7[11] | $2.30 \times 10^{-4}$ | 25 | 25 | 20 | 15 |
| $C_{12}ESO$ | n-Octane | 8[11] | $7.58 \times 10^{-4}$ | 32 | 30 | 25 | 22 |
| $C_{12}ESO$ | n-Nonane | 9[11] | $3.21 \times 10^{-4}$ | 38 | 35 | 31 | 30 |
| $C_{12}ESO$ | n-Decane | 10[11] | $5.58 \times 10^{-4}$ | 45 | 45 | 40 | 30 |

Example 2: Interfacial Tensions (IFT) Measurements by Spinning Drop Tensiometer

Figure 2:
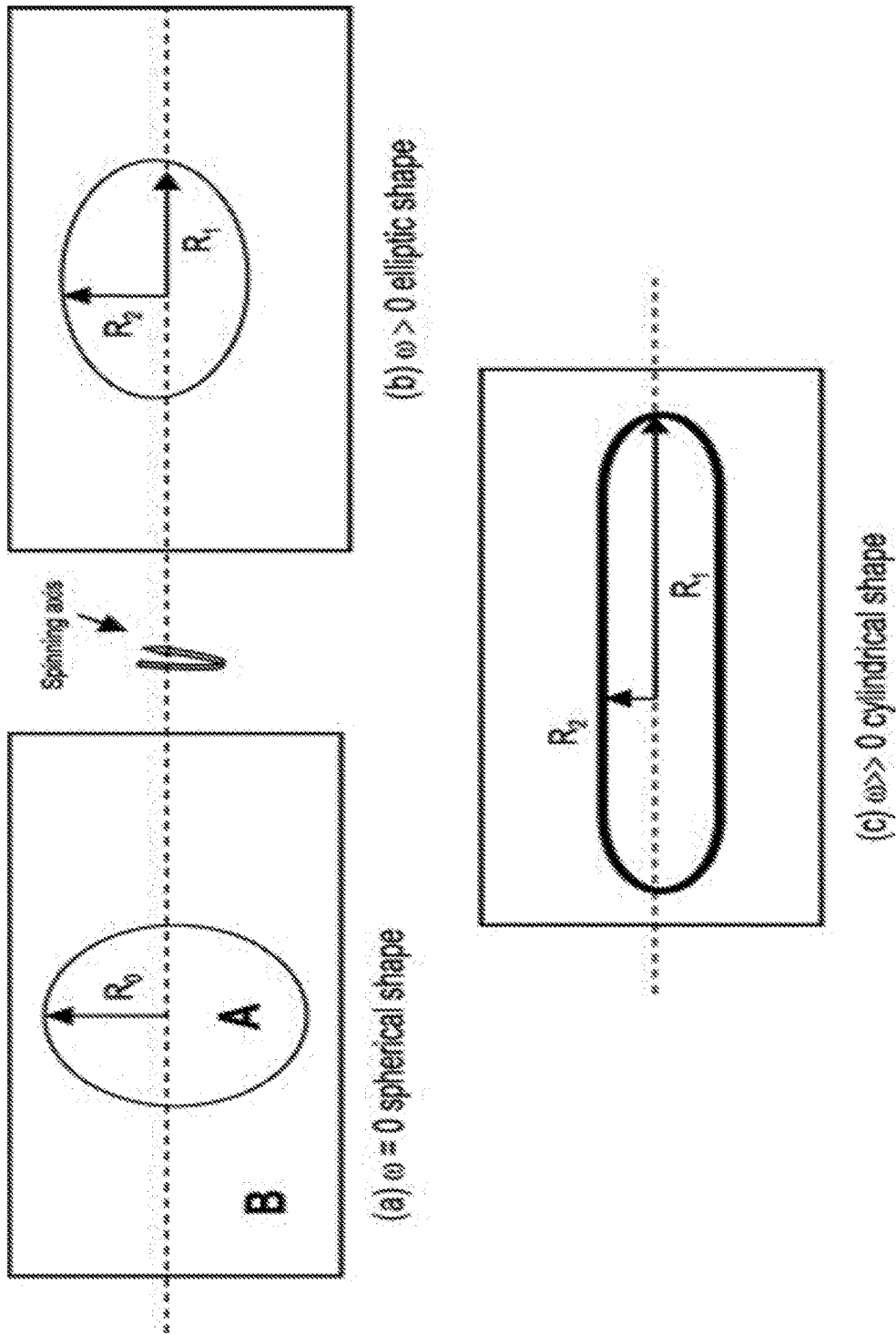
FIG. 2 depicts an illustration of relations between spinning and droplet shape in spinning drop tensiometry.

For a nonionic surfactant/water/oil system, the optimum temperature where equal volumes of oil and water are in the middle phase (Type III) microemulsion is usually close to the medium point of the I/III and III/II PIT. It should be confirmed with interfacial tension (IFT) measurement; the minimum IFT occurs at the optimum temperature. The IFT measurements are performed with a spinning drop tensiometer. The principle of spinning drop measurements is illustrated in FIG. 2. The idea is to measure the radius of the spinning drop ($R_m$) at certain angular velocity ($\omega$), and calculate the IFT with Equation 3 (Vonnegut Formula):

$$\gamma = \Delta\rho \cdot \omega^2 R_m^2/4 \quad \text{Equation 3}$$

IFT measurements for $C_{10}SO$ and $C_{12}SO$ with various hydrocarbons are shown in FIG. 3A and FIG. 3B, respectively. Table 3 show the equivalent alkane carbon number (EACN) of oils, the PIT, and the $IFT_{min}$.

TABLE 3

Optimum temperature and minimum IFT of $C_{10}ESO$ and $C_{12}ESO$ with various alkanes based on IFT measurements.

| Surfactant | Oil | EACN | PIT (° C.) | $IFT_{min}$ (mN/m) |
|---|---|---|---|---|
| $C_{10}ESO$ | Cyclohexane | 2.2 | 21.1 | $1.6 \times 10^{-3}$ |
| $C_{10}ESO$ | Methylcyclohexane | 3.2 | 27.8 | $2.3 \times 10^{-3}$ |
| $C_{10}ESO$ | Ethylcyclohexane | 3.8 | 40 | $2.1 \times 10^{-3}$ |
| $C_{10}ESO$ | Propylcyclohexane | 5.6 | 50 | $9.3 \times 10^{-3}$ |
| $C_{12}ESO$ | n-Hexane | 6 | 15.0 | $1.0 \times 10^{-3}$ |
| $C_{12}ESO$ | n-Heptane | 7 | 18.9 | $2.3 \times 10^{-4}$ |
| $C_{12}ESO$ | n-Octane | 8 | 30.0 | $7.5 \times 10^{-4}$ |
| $C_{12}ESO$ | n-Nonane | 9 | 35.0 | $3.3 \times 10^{-4}$ |
| $C_{12}ESO$ | n-Decane | 10 | 43.9 | $5.8 \times 10^{-4}$ |

The IFT of these systems are in the ultralow range (<10-2 mN/m), therefore having very high solubilization ratio (SP=Mass of maximum solubilized oil/Mass of total surfactant) according to Chun Huh relationship.

$$SP^{-2} \propto IFT \qquad \text{Equation 4}$$

Especially, all the IFTs are in the $10^{-4}$-$10^{-3}$ range (very low even in nonionic surfactant microemulsions), which makes $C_{10}ESO$ and $C_{12}ESO$ good candidates for emulsifiers and cleaning agents.

Example 3: Hydrophilic-Lipophilic Difference (HLD) Parameters

Salager et al. [5-6] first proposed the HLD concept as the thermodynamically derived correlation to describe microemulsion systems. The Hydrophilic-Lipophilic Difference (HLD) equation is a semi-empirical equation that describes the combination of conditions that lead to the phase inversion point. The HLD equation has two general forms for ionic (Equation 1) and nonionic surfactants (Equation 2).

$$\text{Ionic HLD} = Cc + \ln(S) - K(EACN) - f(A) - \alpha_T(\Delta T) \qquad \text{Equation 1}$$

$$\text{Nonionic HLD} = Cc + b^*S - K(EACN) - f(A) + c_T(\Delta T) \qquad \text{Equation 2}$$

Each term can be interpreted in terms of a set of molecular interactions. In Equation 2, Cc is the characteristic curvatures of surfactant which reflects the hydrophilic/lipophilic nature of the surfactant. The term ln(S) is the logarithm of the concentration of the electrolyte (in g/100 ml); this factor represents the charge "shielding" effect of electrolyte due to the contraction of the double layer. EACN is the equivalent alkane carbon number which is analogous to the ACN (Alkane Carbon Number) and indicates the hydrophobicity of the oil phase. For primary alkanes, EACN is the number of hydrocarbon units. For oils other than primary alkanes, EACN is a characteristic number of the oil often determined by microemulsion test although this parameter can be calculated using Hansen solubility parameters [7]. K is an empirical constant depending on the type of surfactant head group. The value of K ranges from 0.1 to 0.2 for numerous surfactants—oil combinations, but a value of 0.17 is typically used for most surfactants [8-9]. f(A) is a function that depends on the concentration of alcohol or more generally a cosurfactant (zero if none added as was the case in this study), The temperature factor, $\alpha_T$, is typically 0.01 K-1, and $\Delta T$ is T-Tref, where T is the temperature of the system and Tref is the reference temperature (25° C.). The factor $\alpha_T(\Delta T)$ reflects the weakening of the hydrogen bonds between water molecules when the temperature of the system increases. If there is any hydrogen bonding in the surfactant (for example alcohol ether sulfates) then $\alpha T$ will be different.

For Equation 2 which applies to nonionic ethoxylated surfactants, the term Cc once again represents the characteristic curvature for the surfactant. The term b*S accounts for the "salting out" of the nonionic surfactant from the aqueous phase when the electrolyte concentration increases. K*EACN and $c_T(\Delta T)$ have the same meaning as with ionic surfactants, except cT is much larger (generally 0.06 K-1 [8-9]) because of the hydrogen bonding. The large cT is due to the weakening of the hydrogen bonds between the molecules of water and the oxygen in the ethylene oxide groups of surfactant molecule when the temperature increases.

The characteristic curvature (Cc) as a term was introduced by Acosta et al. [8], as an extension of the original surfactant parameter σ in the HLD, that quantifies the lipophilic and hydrophilic nature of the surfactant [10]. Cc describes not only the hydrophilic/lipophilic nature of a surfactant, but the type of nanostructures the surfactant is likely to form at the reference conditions. Negative values of Cc represent a hydrophilic surfactant that tends to form oil-swollen micelles, while positive Cc values represent a lipophilic surfactant that tends to form water-swollen reverse micelles.

HLD=0 represents the phase inversion point where bi-continuous network of oil and water channels has been formed (Type III microemulsion). At HLD=0, the interfacial tension tends to reach ultralow values, the emulsion stability is reduced to a minimum, changes in oil and water solubilization capacity, viscosity, and detergency performance take place. Because of these characteristics, the microemulsion is said to be at its optimum state. Positive values of HLD indicate water-swollen reverse micelles dispersed in an oil continuous phase (w/o, Type II microemulsion) while negative values of HLD indicate oil-swollen micelles dispersed in a continuous aqueous phase (o/w Type I microemulsion).

Once the PITs of one surfactant vs. various oils are obtained in the absence of salt, the parameters cT/K and Cc/K can be obtained from the linear regression of EACN vs. PIT when S=0 and f (A)=0 in the HLD equation:

$$EACN = c_T/K \cdot (PIT-25) + Cc/K \qquad \text{Equation 1}$$

Cc/K is known as the optimum EACN of an emulsifier; this ratio is equal to the EACN of the oil that forms an optimum microemulsion with the target surfactant at 25° C. with pure water. $c_T/K$ is the PIT dependence of EACN for a target surfactant. Determination of the individual K, cT and Cc is not possible from Equation 5.

With HLD=0 and with salt added four unknowns, b, Cc, CT and K, arise from Equation 3. These four parameters can be obtained for ester sulfoxides using an error minimization procedure if enough (at least four) different oil/salt combinations can be found that form middle phase microemulsions with ester sulfoxides.

Figure 4:
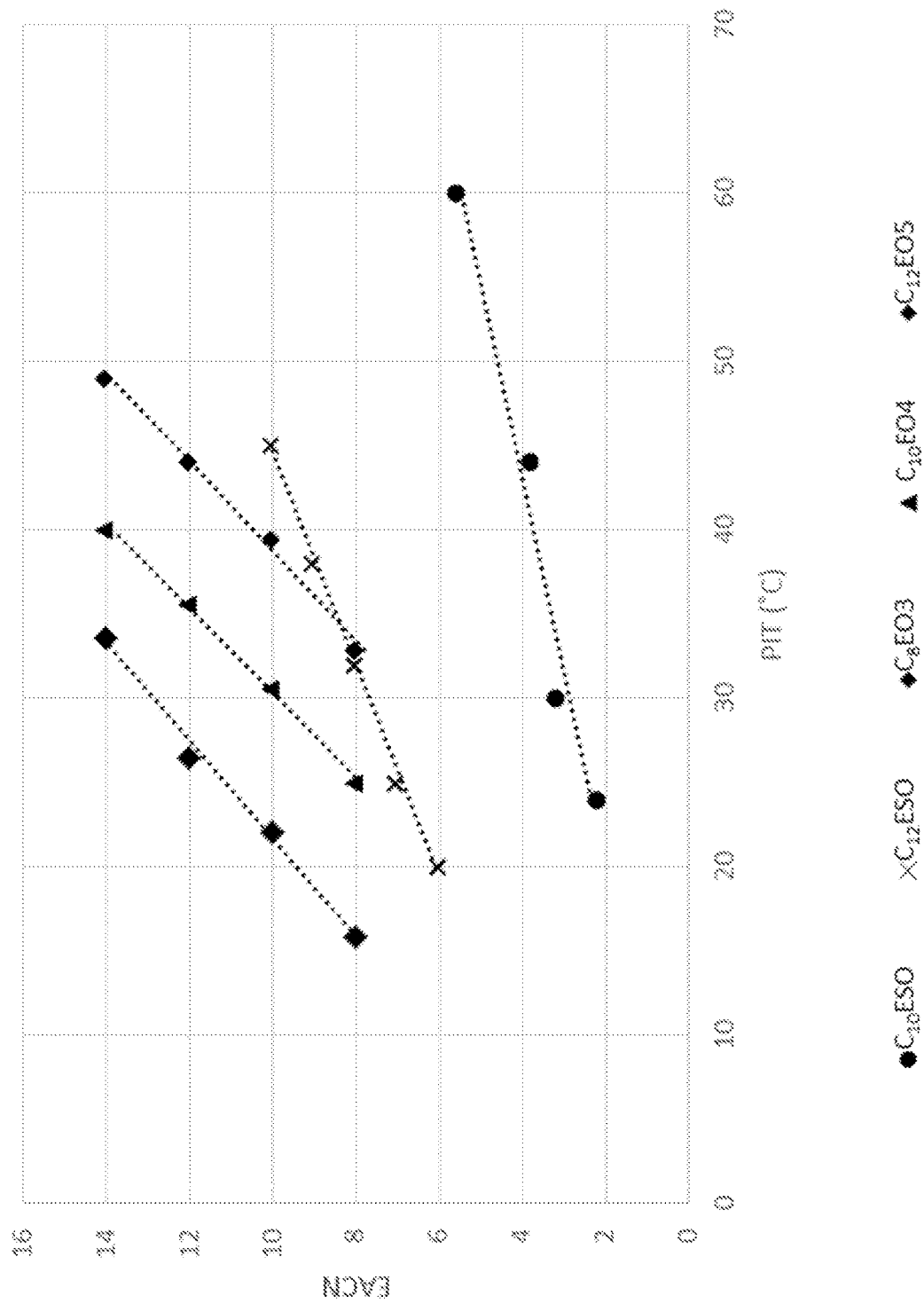
FIG. 4 depicts EACN vs. PIT curves for $C_{10}ESO$ and $C_{12}ESO$ in comparison with various AE surfactants.

By doing a simple linear regression of the EACN vs. PIT data in the absence of salt according to the Equation 1, the parameters $c_T/K$ and Cc/K were obtained from the slope and the intercept of the line respectively, see data in Table 4. EACN vs. PIT data of $C_{10}ESO$ and $C_{12}ESO$ in comparison with various alcohol ethoxylate surfactants by Sottman and Strey [3] are fitted with lines as presented in FIG. 4. Both the sulfoxide surfactants presented lower $c_T/K$ than AE surfactants, which means the PITs are more sensitive to a change in EACN for the latter.

TABLE 4

HLD parameters of $C_{10}ESO$ and $C_{12}ESO$ compared with three AE surfactants[11]

| Surfactant | $c_T/K$ | Cc/K |
|---|---|---|
| $C_{10}ESO$ | 0.087 | 2.43 |
| $C_{12}ESO$ | 0.16 | 6.89 |
| $C_8EO_3$ | 0.34 | 11.17 |
| $C_{10}EO_4$ | 0.39 | 7.90 |
| $C_{12}EO_5$ | 0.37 | 4.89 |

To find the four unknowns in Equation 3 for the ester sulfoxides, PITs of sixteen microemulsions of $C_{10}ESO$ (four oils with four concentrations of brine) and twenty microemulsions of $C_{12}ESO$ (five oils with four concentrations of brine) were found experimentally. The S values for each microemulsion were substituted in equation according to the concentration of the brine used. EACNs of the oils used in each microemulsion and PITs ($\Delta T$=PIT-25) were substituted in equation 3 accordingly while HLD was equated to zero. This resulted in a system of sixteen sets of homogeneous equations for $C_{10}ESO$ surfactant and twenty sets of homogeneous equations for $C_{12}ESO$ surfactant. The trivial solution (i.e. all adjustable parameters=0) to sets of homogeneous equations obviously does not provide the ester sulfoxide parameters. The nontrivial solution could not be found for this system of equations since the coefficient matrix is not a singular matrix i.e. a solution to make all HLDs equations exactly equal to zero could not be found. Hence a numerical method instead of matrix method was used to solve for unknowns.

The K, Cc, CT and b variables were varied in the ranges $0.1<K<0.3$, $-14<Cc<14$, $0<cT<2$, $0<b<3$ accordingly and the absolute values of the all individual HLD equations were minimized simultaneously. The HLD parameters were obtained such that the sum of absolute values of the HLD parameters were minimized.

Values for b, Cc, CT and K were obtained and presented in Table 5. The Cc value of $C_{12}ESO$ was found to be higher than that of $C_{10}ESO$ which shows $C_{12}ESO$ is more hydrophobic than the $C_{10}ESO$ as expected. b was found to be 0.01 for $C_{10}ESO$ and 0.02 for $C_{12}ESO$. K was found 0.10 for $C_{10}ESO$ and 0.12 for $C_{12}ESO$ surfactants. cT was found to be 0.01 K-1 for $C_{10}ESO$ and 0.02 K-1 for $C_{12}ESO$. The dependence of the temperature for optimal microemulsion or cT is substantially less for sulfoxide surfactants compared to ethylene oxide surfactants and is essentially equivalent to the value for ionic surfactants. Specifically, the reported cT value for AEs has been measured as 0.061[3] and did not change with a change in aliphatic chain length.

TABLE 5

CT and Cc of $C_{10}ESO$ and $C_{12}ESO$ compared with three AE surfactants[11]

| Surfactant | $C_T$ | Cc | b | k |
|---|---|---|---|---|
| $C_{10}ESO$ | 0.01 | 0.24 | 0.01 | 0.10 |
| $C_{12}ESO$ | 0.02 | 0.82 | 0.02 | 0.12 |
| $C_8EO_3$ | 0.061 | 1.9 | — | 0.1-0.2 |
| $C_{10}EO_4$ | 0.063 | 1.4 | — | 0.1-0.2 |
| $C_{12}EO_5$ | 0.061 | 0.87 | — | 0.1-0.2 |

Based on Cc, the indicator of surfactant hydrophobicity at 25° C. with no added salt, $C_{12}ESO$ (Cc=0.82) is almost equally hydrophobic to $C_{12}EO_5$ (Cc=0.87)[11], indicating that 1 ester sulfoxide (ESO) unit is as essentially as hydrophilic as 5 EO groups. Since $C_{12}EO_6$ has a Cc of –0.2, a linear interpolation for this one sample indicates that ESO is equivalent exactly to 4.90 EO groups. A similar comparison done between $C_{10}ESO$ (Cc=0.24) and $C_{10}EO_5$ (Cc=0.1), also shows that 1 ESO unit is essentially as hydrophilic as 5 EO groups. Linear interpolation with $C_{10}EO_4$ (Cc=1.4) gives a value that ESO is equal to 4.87 EO groups.

REFERENCES FOR EXAMPLES 1-3

1. Shinoda, K., Arai, H., (1964), The correlation between phase inversion temperature in emulsion and cloud point in solution of nonionic emulsifier *The Journal of Physical Chemistry*, 68, pp. 3485-3490.
2. Huh, C., (1979), Interfacial tensions and solubilizing ability of a microemulsion phase that coexists with oil and brine. *Journal of Colloid and Interface science*, 71, pp. 408-426.
3. Sottmann, T., Strey, R., (1997), Ultra low interfacial tensions in water-n-alkane-surfactant systems. *J Chem Phys*, 106, pp. 8606-8615.
4. Marquez, N., Graciaa, A., Lachaise, J., Salager, J. L., (2002), Partitioning of ethoxylated alkylphenol surfactants in microemulsion-oil-water systems: Influence of physiochemical formulation variables. *Langmuir*, 18, pp. 6021-6024.
5. Salager, J. L., Marquez, N., Graciaa, A, Lachaise, J., (2000), Partitioning of ethoxylated octylphenol surfactants in microemulsion-oil-water systems: Influence of temperature and relation between partitioning coefficient and physiochemical formulation. *Langmuir*, 16, pp. 5534-5539.
6. Salager, J. L., Morgan, J., Schechter, R., Wade, W., Vasquez, E., (1979), Optimum formulation of surfactant/water/oil systems for minimum interfacial tension or phase behavior. *Soc. Pet. Enj. j*, 19, pp. 107-115.
7. Hansen, M, Charles, The three dimensional solubility parameter and solvent diffusion coefficient, Their importance in surface coating formulation. PhD Thesis, Danish Technical Press, 1967
8. Acosta, J. E., Yuan, J. S., Bhakta, A. S., (2008), The characteristic curvature of ionic surfactants. *Journal of Surfactants and Detergents*, 11, pp. 145-158.
9. Acosta, J. E., (2008), The HLD-NAC equation of state for microemulsions formulated with nonionic alcohol ethoxylate and alkylphenol ethoxylate surfactants. *Colloid and Surfaces A: Physiochemical and Engineering Aspects*, 320, pp. 193-204.
10. Bourrel, M., Salager, J. I., Schechter, R. S., Wade, W. H., (1980), A correlationn for phase behavior of nonionic surfactants. *J Colloid Interface Sci*, 75, pp. 451-461.
11. Bourrel, M., Schechter, R. S., Microemulsions and related systems: formulation, solvency and physical properties. 1988, New York: M. Dekker.
12. Bouton, F. O., Durand, M., Nardello-Rataj, V., Borosy, A., Quellet, C., Aubry, J. M., (2010), A QSPR model for the prediction of the "Fish-tail" temperature of CiE4/water/polar hydrocarbon oil systems. *Langmuir*, 26, pp. 7962-7970.
13 Queste, S., Salager, J. L., Strey, R., Aubry, J. M., (2007), The EACN scale for oil classification revisited thanks to fish diagram. *Journal of Colloid and Interface Science*, 312, pp. 98-107

What is claimed is:

1. A microemulsion comprising at least one surfactant, an oil phase, and an aqueous phase, wherein the surfactant is a compound of Formula (IV) or Formula (IVa):

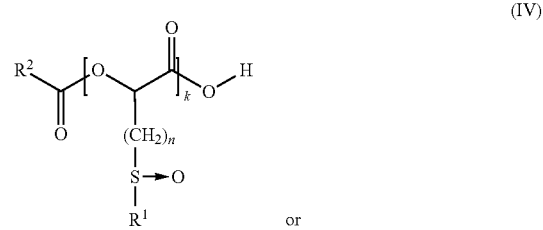

or

-continued

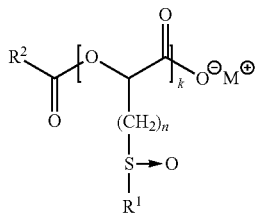
(IVa)

wherein
R¹ is $C_1$-$C_6$ alkyl;
R² is $C_{10}$-$C_{30}$ alkyl or $C_8$-$C_{30}$ alkenyl;
M is a cation chosen from ammonium, an alkali metal, an alkaline earth metal, or a transition metal;
k is an integer from 1 to 10;
and
n is an integer from 1 to 3;
wherein the microemulsion has an interfacial tension from about $6\times10^{-4}$ mN/m to about $10\times10^{-2}$ mN/m.

2. The microemulsion of claim 1, wherein R¹ is methyl, and n is 2.

3. The microemulsion of claim 1, wherein M is an alkali metal, R¹ is methyl, and n is 2.

4. The microemulsion of claim 1, wherein the oil phase comprises at least one hydrocarbon solvent.

5. The microemulsion of claim 4, wherein the at least one hydrocarbon solvent is selected from the group consisting of hexane, n-hexane, heptane, n-heptane, octane, n-octane, nonane, n-nonane, decane, n-decane, cyclopentane, cyclohexane, cycloheptane, cyclooctane, methyl cyclohexane, ethyl cyclohexane, propyl cyclohexane, and combinations thereof.

6. The microemulsion of claim 5, wherein the at least one hydrocarbon solvent is selected from the group consisting of cyclohexane, methyl cyclohexane, ethyl cyclohexane, and propyl cyclohexane.

7. The microemulsion of claim 5, wherein the at least one hydrocarbon solvent is selected from the group consisting of hexane, heptane, octane, nonane, and decane.

8. The microemulsion of claim 1, wherein the oil phase is present in the microemulsion in an amount from about 1% (v/v) to about 99% (v/v).

9. The microemulsion of claim 1, wherein the aqueous phase comprises at least one aqueous liquid selected from the group consisting of water, distilled water, purified water, de-ionized water, tap water, salt solutions, and combinations thereof.

10. The microemulsion of claim 9, wherein the at least one aqueous liquid is water.

11. The microemulsion of claim 9, wherein the at least one aqueous liquid is a salt solution.

12. The microemulsion of claim 11, wherein the salt solution comprises an alkali metal salt or an alkaline earth metal salt.

13. The microemulsion of claim 12, wherein the salt solution comprises sodium chloride.

14. The microemulsion of claim 1, wherein the aqueous phase is present in the microemulsion in an amount from about 1% (v/v) to about 99% (v/v).

* * * * *